(12) United States Patent
Shibata et al.

(10) Patent No.: US 7,974,721 B2
(45) Date of Patent: Jul. 5, 2011

(54) FABRICATION AIDING APPARATUS

(75) Inventors: Tsutomu Shibata, Tokyo (JP);
Yoshinori Matsuda, Tokyo (JP)

(73) Assignee: GC Corporation, Tokyo (JP)

( * ) Notice: Subject to any disclaimer, the term of this patent is extended or adjusted under 35 U.S.C. 154(b) by 1178 days.

(21) Appl. No.: 11/705,596

(22) Filed: Feb. 13, 2007

(65) Prior Publication Data
US 2007/0203599 A1 Aug. 30, 2007

(30) Foreign Application Priority Data

Feb. 15, 2006 (JP) .................................. 2006-038022

(51) Int. Cl.
*G06F 19/00* (2006.01)
*A61C 5/10* (2006.01)
*G09G 5/00* (2006.01)
*G06G 7/58* (2006.01)

(52) U.S. Cl. .......... 700/98; 700/182; 433/223; 345/581; 345/441; 703/11

(58) Field of Classification Search .................. 700/97, 700/98, 118–120, 180, 182; 345/419, 420, 345/581, 441–443; 433/223, 229; 703/6, 703/7, 11
See application file for complete search history.

(56) References Cited

U.S. PATENT DOCUMENTS

| 5,417,572 A * | 5/1995 | Kawai et al. ................. 433/218 |
| 2006/0183082 A1* | 8/2006 | Quadling et al. ............. 433/223 |

FOREIGN PATENT DOCUMENTS

| JP | 5-269146 | 10/1993 |
| JP | 2000-185060 | 7/2000 |
| JP | 3460741 | 8/2003 |

* cited by examiner

*Primary Examiner* — Sean P Shechtman
(74) *Attorney, Agent, or Firm* — McGinn IP Law Group, PLLC

(57) ABSTRACT

A fabrication aiding apparatus capable of easily and properly setting a margin line is provided. The apparatus includes a RAM (Random Access Memory) to store three-dimensional shape data on a model of an abutment tooth to which a dental prosthesis is applied, an accepting section to accept the input of specification of an angle formed between a line defining a contact point and a reference axis on a face containing the reference axis in the model, a contact point detecting section to detect, based on the three-dimensional shape data, three-dimensional position information about a contact with the line forming a specified angle with the reference axis on the face containing the reference axis in the model, and a margin determining section to determine, based on coordinates of a contact point, three-dimensional position information of a margin line in the model.

16 Claims, 17 Drawing Sheets

FABRICATION AIDING APPARATUS

BACKGROUND OF THE INVENTION

1. Field of the Invention

The present invention relates to a fabrication aiding apparatus configured to aid the fabrication of a dental prosthesis such as an inlay, crown, bridge or a like.

2. Description of the Related Art

A conventionally known method for fabricating a dental prosthesis such as an inlay, crown, bridge, or a like includes a method of casting a metal material using a so-called lost wax casting method, a method of forming a ceramic material on a refractory cast and then baking the formed ceramic material using a vacuum electric furnace to fabricate a prosthesis, or a like.

However, to fabricate a dental prosthesis by using the lost wax casing method or the baking method as described, many procedures to be performed manually by a dental technician are required. These procedures present a problem in that they are exact and complicated work, as a result, requiring a lot of process and time. Also, quality of a dental prosthesis varies depending on a degree of skill of a dental technician.

To solve these problems, in recent years, a dental CAD/CAM (Computer Aided Design and Computer Aided Manufacturing) system has been developed in which three-dimensional shape data on a dental prosthesis is created and, based on the three-dimensional data, a dental prosthesis is fabricated by using a machine such as a milling machine, which makes it possible to fabricate a stable-quality dental prosthesis.

In the CAD/CAM, it is important how determine a margin line between an abutment tooth and a dental prosthesis.

When a margin line is set, as a preparatory step, a plaster model containing an abutment tooth to which a dental prosthesis is applied is fabricated. Next, a plaster model is fabricated with its margin portion made clear, to be used for three-dimensional shape measurement. That is, in many cases, a margin portion exists within a gingiva and, therefore, by deleting a dispensable portion corresponding to the gingiva from the plaster model, a model having a clear margin portion to be used for the three-dimensional shape measurement is made. Then, by obtaining three-dimensional shape data from the plaster model, and a margin line is detected from the obtained three dimensional shape data. As methods for detecting and setting a margin line, a method of applying a maximum contour portion as a margin or a method of using a maximum point of inflection on an external contour line as a margin line [see, for example, Patent Reference 1 (Japanese Patent Application Laid-open No. 1993-269146)], or a method of using a shadow produced by illuminating a tooth as a margin line [see, for example, Patent Reference 2 (Japanese Patent Application Laid-open No. 2000-185060)] are known.

In the margin line setting process described above, since a margin line is determined uniformly from the three-dimensional data, if a dental technician fails to form an abutment tooth having a suitable shape or if a dental technician deletes erroneously an appropriate portion when fabricating a model, there is a fear of a failure in properly setting a margin line.

To solve this problem, technology by which an operator of a CAD system can freely set a margin line is known [see, for example, Patent Reference No. 3 (Japanese Patent NO. 3460741). According to this technology, a longitudinal cross-sectional diagram of an original model body of a tooth or a like is displayed on a screen and a margin portion is determined by an operator on the longitudinal cross-sectional diagram and then a plurality of the longitudinal cross-sectional diagrams of a plurality of original model bodies is displayed for the specification of the margin portions and respective margin portions are connected so as to be joined to set a margin line.

However, the above-described technology by which an operator of a CAD system can freely set a margin line has a problem. That is, it is necessary that the procedures in which the operator sets an appropriate margin portion while watching each cross-sectional diagram are repeated a plurality of times (for example, 36 times), which requires a lot of work and time of the operator. Moreover, when a margin portion is to be set on each cross-sectional diagram, accurate indication of a margin portion by using an input device such as a mouse is necessary, which requires delicate and exact work and skill of an operator, as a result, imposing a load on the operator.

SUMMARY OF THE INVENTION

In view of the above, it is an object of the present invention to provide a technology by which a suitable margin line can be easily set.

According to a first aspect of the present invention, there is provided a fabrication aiding apparatus including:

a shape data storing means to store three-dimensional shape data on a model of an abutment tooth to which a dental prosthesis is applied, an angle input accepting means to accept an input of specification of an angle formed between a line defining a contact point and a reference axis on a face containing the reference axis in the model, a contact point detecting means to detect, based on the three-dimensional shape data, three-dimensional position information about a contact point with the line which forms a specified angle with the reference axis on a face containing the reference axis in the model, and a margin line determining means to determine, based on coordinates of the contact point, three-dimensional position information about a margin line in the model of the abutment tooth.

By configuring as above, by specifying an angle formed with the reference axis, three-dimensional position information about a margin line based on the contact point having the specified angle can be determined. Therefore, by adjusting the specified angle, a margin line can be easily and properly determined.

In the foregoing, a preferable mode is one that wherein includes a detecting range input accepting means to accept an input of a detecting range in which the contact point with the line having the specified angle in the model of the abutment tooth is detected.

By configuring as above, a contact point with a line having a specified angle is detected to determine a margin line in a specified range.

Also, a preferable mode is one that wherein includes a display means to stereoscopically display the model on a display device based on the three-dimensional data, wherein the detecting range input accepting means accepts an input of specification of the detecting range according to a mark on the model stereoscopically displayed.

By configuring as above, an operator can specify a detecting range while checking a model displayed stereoscopically and can easily and properly determine a margin line.

Also, a preferable mode is one wherein the detecting range input accepting means accepts an input of a detecting range in a direction of the reference axis.

By configuring as above, processing of detecting a contact point only within the detecting range in the direction of the reference axis is enough, thus resulting in reduction of an amount of processing.

Also, a preferable mode is one wherein the contact point detecting means detects a contact point by judging whether or not a plurality of points of the model that belong to the detecting range in the reference axis direction on a face containing the reference axis is a contact point with the tangential line having the angle.

By configuring as above, judgement of whether only a plurality of points within the detecting range in the direction of the reference axis is a contact point or not is enough, thus resulting in reduction of an amount of processing.

Also, a preferable mode is one wherein the contact point detecting means determines a line to be used for calculation that exists on a side of the model being inner than the plurality of points and that forms the angle with the reference axis and detects a point being farthest from the line to be used for calculation as the contact point from the plurality of points of the model that belong to a detecting range in the reference axis direction.

By configuring as above, a contact point can be detected by calculating a distance between each of the plurality of points and the line for calculation.

Also, a preferable mode is one wherein the detecting range input accepting means accepts an input of a detecting range in a direction surrounding the reference axis.

By configuring as above, a contact point with a specified line can be detected within a detecting range in the direction surrounding the reference axis.

Also, a preferable mode is one wherein the angle input accepting means to accept an input of specification of a plurality of angles, the detecting range input accepting means accepts an input of each of detecting ranges in a direction surrounding the reference axis in which a contact point with the line having each of the specified angles is detected, the contact point detecting means detects a contact point with the line having each of the specified angles, and the margin line determining means determines three-dimensional position information about a margin line in the model of the abutment tooth based on the contact point detected within each of the detecting range.

By configuring as above, in a plurality of detecting ranges in the direction surrounding the reference axis, different angles formed by the line defining each of contact points in each of the detecting range can be specified and a margin line can be determined based on these contact points. Thus, a margin line desired by an operator can be easily determined in the direction of the reference axis.

According to a second aspect of the present invention, there is provided a fabrication aiding method to be applied to a fabrication aiding apparatus that aids fabrication of a dental prosthesis having a shape data storing means to store three-dimensional shape data on a model of an abutment tooth to which the dental prosthesis is applied, the method including:

an angle input accepting step of accepting an input of specification of an angle formed between a line defining a contact point and a reference axis on a face containing the reference axis in the model;

a contact point detecting step of detecting, based on the three-dimensional shape data, three-dimensional position information about a contact with the line which forms a specified angle with the reference axis on a face containing the reference axis in the model; and a margin line determining step of determining, based on coordinates of the contact point, three-dimensional position information of a margin line in the model of the abutment tooth.

By configuring as above, three-dimensional position information about a margin line based on a contact point with a line having the specified angle can be determined by calculating an angle with the reference axis.

According to a third aspect of the present invention, there is provided a fabrication aiding program to be executed by a computer making up a fabrication aiding apparatus to aid fabrication of a dental prosthesis wherein the fabrication aiding apparatus includes a shape data storing means to store three-dimensional shape data on a model of an abutment tooth to which the dental prosthesis is applied, wherein the fabrication aiding program makes the computer function as an angle input accepting means to accept an input of specification of an angle formed between a line defining a contact point and a reference axis on a face containing the reference axis in a model, function as a contact point detecting means to detect, based on the three-dimensional shape data, three-dimensional position information about a contact with the line which forms a specified angle with the reference axis on a face containing the reference axis in the model, and further function as a margin line determining means to determine, based on coordinates of the contact point, three-dimensional position information of a margin line in the model of the abutment tooth.

By configuring as above, when the program is made to be executed by the computer, three-dimensional position information about a margin line based on a contact point with the line having the angle by specifying an angle formed by the reference axis can be determined. Therefore, by adjusting a specified angle, a margin line can be easily and properly determined.

BRIEF DESCRIPTION OF THE DRAWINGS

The above and other objects, advantages, and features of the present invention will be more apparent from the following description taken in conjunction with the accompanying drawings in which.

DETAILED DESCRIPTION OF THE PREFERRED EMBODIMENTS

Best modes of carrying out the present invention will be described in further detail using various embodiments with reference to the accompanying drawings. The following embodiments do not restrict the inventions stated in claims and all the combinations of features described in the embodiments are not necessarily essential as solving means of the invention.

Figure 1:
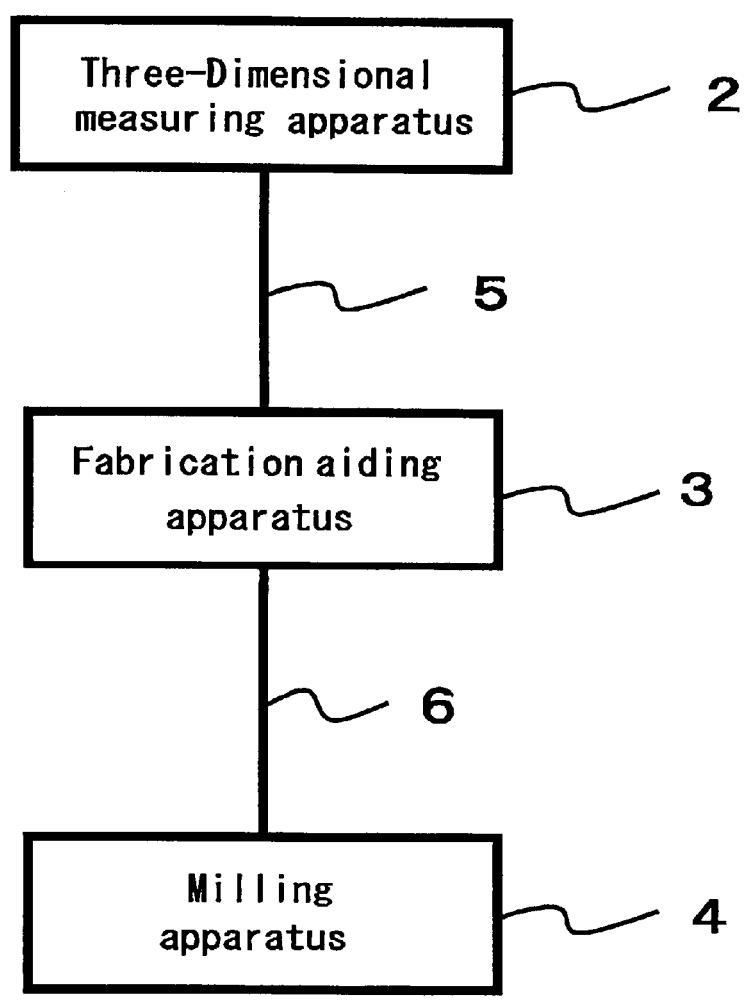
FIG. 1 is a diagram showing configurations of a dental prosthesis fabricating system according to an embodiment of the present invention.

First, configurations of a dental prosthesis fabricating system 1 according to an embodiment of the present invention is described. FIG. 1 is a diagram showing configurations of a dental prosthesis fabricating system according to an embodiment of the present invention. The dental prosthesis fabricating system 1 includes a three-dimensional measuring apparatus 2, a fabrication aiding apparatus 3, and a milling apparatus 4. The three-dimensional measuring apparatus 2 and the fabrication aiding apparatus 3 are connected to each other by a cable 5 such as a USB (Universal Serial Bus) cable or a like and data is transmitted or received between the two apparatuses. The fabrication aiding apparatus 3 and the milling apparatus 4 are connected to each other by a cable 6 such as a USB cable or a like and data is transmitted or received between the two apparatuses.

The three-dimensional measuring apparatus 2 creates three-dimensional shape data on a model of an abutment tooth by measuring the model of the abutment tooth by, for example, a laser three-dimensionally and transmits the obtained data to the fabrication aiding apparatus. The three-dimensional measuring apparatus 2 uses, for example, an axis passing through a center of a model and approximately corresponding to a direction (in the case of a natural tooth, it is a direction of eruption) in which an abutment tooth faces as a reference axis in a Z direction at time of the measurement and chooses an X-axis and Y-axis being vertical to each other in a face being vertical to the reference axis to create three-dimensional shape data using three-dimensional_coordinates formed by these three axes X, Y and Z. The fabrication aiding apparatus 3 is made up of, for example, a PC (Personal Computer) or a like and performs processing of creating fabricating data to be used for the fabrication of a dental prosthesis to be suitably applied to an abutment tooth, according to a promoting input from an operator, by using the three-dimensional data fed from the three-dimensional measuring apparatus 2 and transmits the created fabricating data to the milling apparatus 4. The milling apparatus 4 fabricates a dental prosthesis by milling a material such as a ceramic according to the fabricating data transmitted from the fabrication aiding apparatus 3.

Figure 2:
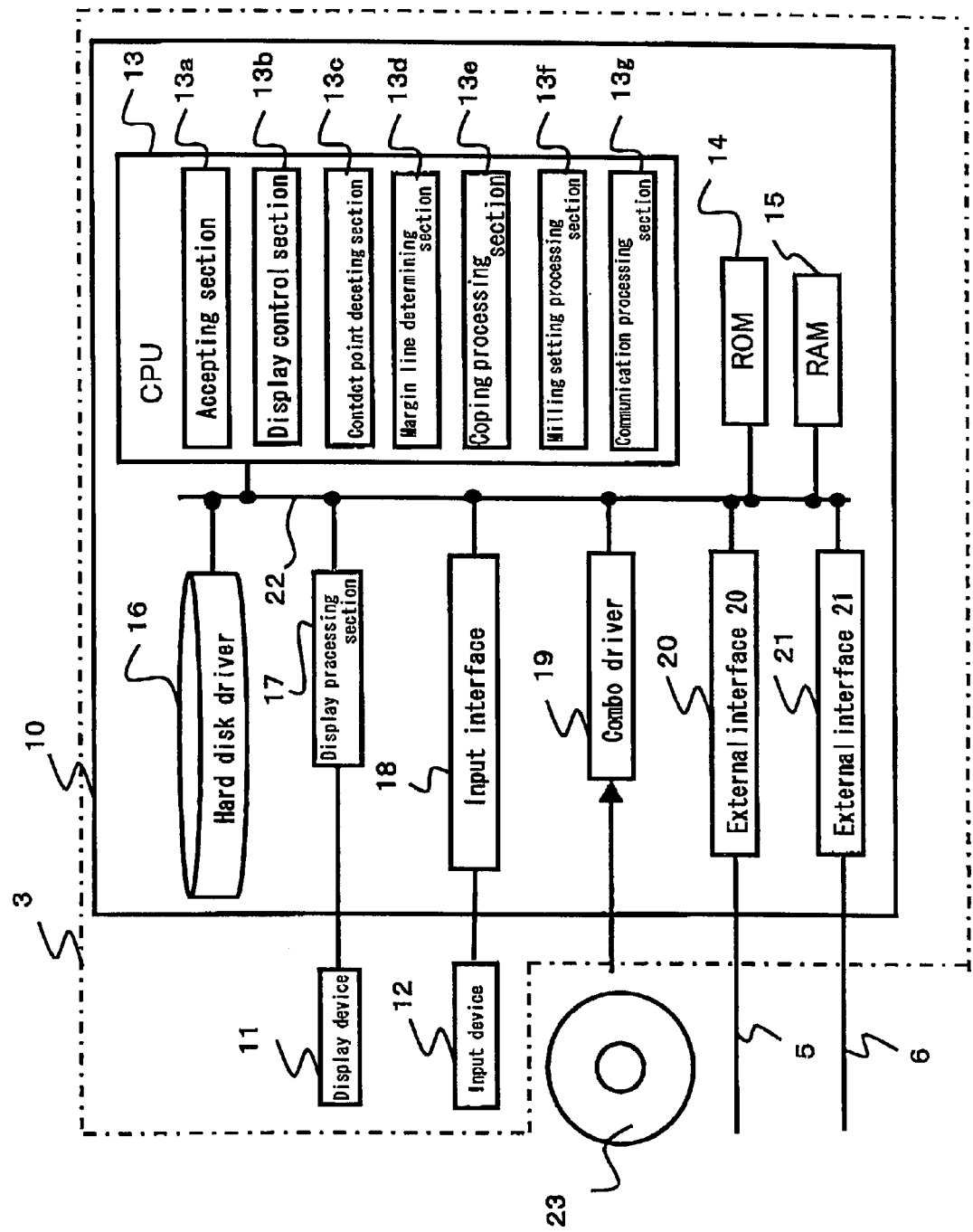
FIG. 2 is a diagram showing configurations of a fabrication aiding apparatus according to the embodiment of the present invention.

Next, the fabrication aiding apparatus 3 is described in detail below. FIG. 2 is a diagram showing configurations of the fabrication aiding apparatus of the embodiment of the present invention. The fabrication aiding apparatus 3 includes an apparatus main body 10, a display device 11, and an input device 12. The display device 11 is a device to display images such as a liquid crystal display device, a CRT (Cathode Ray Tube) display or a like. The input device 12 is a device to accept an input from an operator of the fabrication aiding apparatus 3 such as a mouse, keyboard, or a like. In the apparatus main body 10, a CPU (Central Processing Unit) 13, a ROM (Read Only Memory) 14, a RAM (Random Access Memory) 15, a hard disk driver 16, a display processing section 17, an input interface 18, a combo driver 19, an external interface 20 and an external interface 21 are connected one another via a bus 22.

The ROM 14 stores a basic program such as a boot program. The RAM 15 is used as an area in which a program or data is stored or as a working area in which data being used for processing by the CPU 13 is stored. In the present embodiment, the RAM 15 is one example of a form data storing means and stores three-dimensional data of an abutment tooth to be processed. Also, in the present embodiment, the RAM 15 is one example of a margin line storing means and stores three-dimensional position information about a margin line set in the processing. The display processing section 17 creates display data to make images be displayed on the display device 11 and outputs the created data to the display device 11.

The combo driver 19 reads data and programs from a plurality of storage media 23 and writes data to the storage media 23. Examples of the storage medium are CD (Compact Disk)-ROM, DVD (Digital Versatile Disk)-ROM, DVD-RAM, or a like. The hard disk driver 16 saves an OS (Operating System), various programs and data bases so as to be readable. According to the embodiment, the hard disk driver 16 stores a fabrication aiding program to aid the fabrication of a dental prosthesis and three-dimensional shape data on a plurality of abutment tooth models.

The input interface 18 is configured to be connectable with the input device 12 and to transfer signals fed from the input device 12 as data to the CPU 13 and RAM 15. The external interface 20 serves as a mediator to exchange data with external devices. According to the embodiment, the external interface 20 exchanges data with the three-dimensional measuring apparatus 2 connected via the cable 5. The external interface 21 serves as a mediator to exchange data with external devices. According to the embodiment, the external interface 21 exchanges data with the milling apparatus 4 connected via the cable 6.

The CPU 13 reads a basic program stored in the ROM 14 and an OS or programs stored in the hard disk driver 16 to the RAM 15 and performs various types of processing. The CPU 13 controls operations of each of the above components 14 to 21.

In the present embodiment, the CPU 13 includes an accepting section 13a serving as one example of an angle input accepting means, a detection range input accepting means, and a thickness information input accepting means, a display control section 13b serving as one example of a display means, a contact point detecting section 13c serving as one example of a contact point detecting means, a margin line determining section 13d serving as one example of a margin line determining means, a coping processing section 13e serving as one example of a contour determining means and an entire circumference determining means, a milling setting processing section 13f, and a communication processing section 13g, all of which are driven and operated according to the CPU's execution of the OS and fabrication aiding programs stored in the hard disk driver 16.

The accepting section 13a accepts various instructions to be provided on a variety of windows displayed by the display control section 13b according to operations performed by an operator using the input device 12. Also, in the embodiment, the accepting section 13a accepts various instructions to be provided on a main window 31 (see FIG. 3), a margin line setting window 51 (see FIG. 4), a creation confirming window 57 (see FIG. 5), an inner face setting window 61 (see FIG. 6), a contour setting window 71 (see FIG. 8) according to operations performed by the operator using the input device 12.

The display control section 13b makes the display processing section 17 display a main window 31, a margin line setting window 51, a creation confirming window 57, an inner face setting window 61, and a contour setting window 71 on the display device 11. For example, the display control section 13b performs a process of displaying a stereoscopic image of a model on the display device 11 based on three-dimensional data on a model stored in the RAM 15. Besides, the display control section 13b changes a displayed state of a stereoscopic image of a model in response to operator's instructions already accepted by the accepting section 13a.

Figure 3:
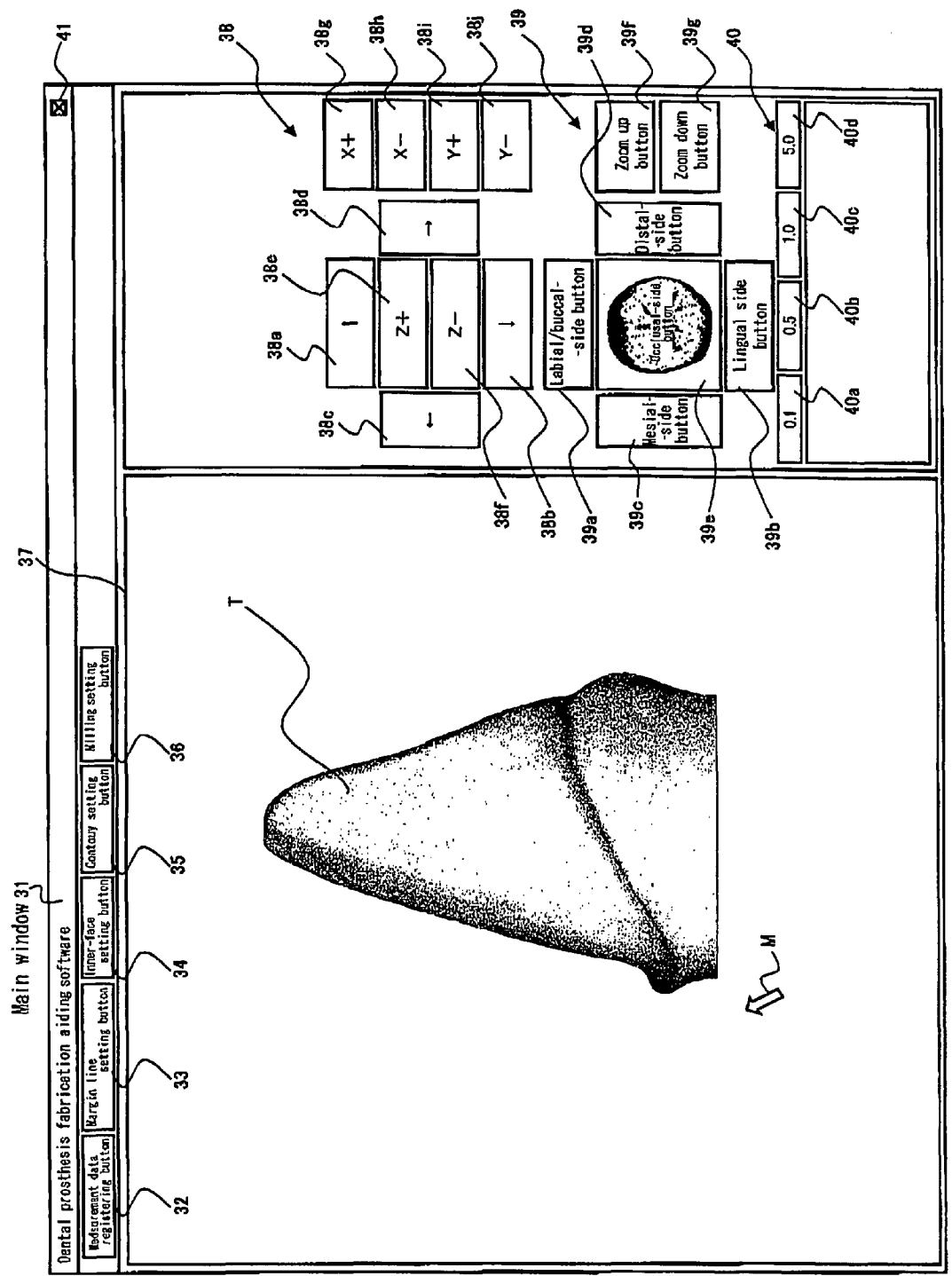
FIG. 3 is a diagram showing a main window according to the embodiment of the present invention.

FIG. 3 is a diagram showing the main window 31 according to the embodiment of the present invention. On the main window 31 are displayed a measurement data registering button 32, a margin line setting button 33, an inner-face setting button 34, a contour setting button 35, a milling setting button 36, an image display region 37, an image moving button 38, an image display direction button 39, a moving amount button 40, and a closing button 41.

The measurement data registering button 32 is a button to accept instructions for starting data registering processing which enables three-dimensional image data on a model of an abutment tooth to aid the fabrication to be processed by using software. The margin line setting button 33 is a button to accept instructions for starting margin line setting processing. The inner face setting button 34 is a button to accept instructions for starting inner-face forming processing. The contour setting button 35 is a button to accept instructions for starting contour creating processing. The milling setting button 36 is a button to accept instructions for starting milling setting processing. The image display region 37 is a region in which a model of an abutment tooth registered by the data registering processing and an image of the model are to be displayed. Moreover, FIG. 3 shows a case in which a model of an abutment tooth to be processed has been registered and the model T of the abutment tooth is displayed as a stereoscopic image.

The image moving button 38 is a button to accept instructions for moving an image of the model T being displayed in the image display region 37 and includes an upper moving button 38a, a lower moving button 38b, a left moving button 38c, a right moving button 38d, a Z plus button 38e, a Z minus button 38f, an X plus button 38g, an X minus button 38h, a Y plus button 38i, and a Y minus button 38j. The upper moving button 38a is a button to accept instructions for moving an image of a model in an upward direction. The lower moving button 38b is a button to accept instructions for moving an image of a model in a downward direction. The left moving button 38c is a button to accept instructions for moving an image of a model in a left direction. The right moving button 38d is a button to accept instructions for moving an image of a model in a right direction.

The Z-plus button 38e is a button to accept instructions for rotating an image of a model in a right direction. The Z-minus button 38f is a button to accept instructions for rotating an image of a model in a left direction. The X-plus button 38g is a button to accept instructions for tilting an image of a model to a frontward side. The X-minus button 38h is a button to accept instructions for tilting an image of a model to a backward side. The Y-plus button 38i is a button to accept instructions for tilting an image of a model to a right side. The Y-minus button 38j is a button to accept instructions for tilting an image of a model to a left side.

The image display direction button 39 is a button to accept instructions for controlling a direction and size of an image of a model being displayed in the image display region 37 and includes a labial/buccal side button 39a, a lingual-side button 39b, a mesial-side button 39c, a distal-side button 39d, an occlusal-side button 39e, an expanding button 39f, and a zoom down button 39g. The labial/buccal side button 39a is a button to accept instructions for making a labial/buccal side of a model be displayed as a front of the model. The lingual-side button 39b is a button to accept instructions for making a lingual side of a model be displayed as a front of the model. The mesial-side button 39c is a button to accept instructions for making a distal side be displayed as a front of the model. The distal-side button 39d is a button to accept instructions for making a distal side of a model be displayed as a front of the model. The occlusal-side button 39e is a button to accept instructions for making an occlusal side of a model be displayed as a front of the model. The expanding button 39f is a button to accept instructions for expanding a model to be displayed. The zoom down button 39g is a button to accept instructions for zoom down a model to be displayed.

The moving amount button 40 is a button to accept the input of a unit of an amount of movement to be used for providing an instruction for setting the moving amount to the image moving button 38 and image display direction button 39. The moving amount button 40 has a 0.1 unit button 40a, a 0.5 unit button 40b, a 1.0 unit button 40c, and a 5.0 unit button 40d. The 0.1 unit button 40a is a button to accept the input of 0.1 unit at time of providing instructions for setting the unit to the image moving button 38 and image display direction button 39. The 0.5 unit button 40b is a button to accept the input of 0.5 unit at time of providing instructions for setting the unit to the image moving button 38 and image display direction button 39. The 1.0 unit button 40c is a button to accept the input of 1.0 unit at time of providing instructions for the movement unit to the image moving button 38 and image display direction 39.

The closing button 41 is a button to accept instructions for terminating processing to be performed by the fabrication aiding program. Pressing down the closing button 41 causes the display controlling section 13b to close the main window.

A cursor M, for example a mouse cursor, can be moved on the window by an operator's manipulation of a mouse being one example of the input device 12 and can point a specified position on the window. Moreover, the cursor M with its shape being changed depending on processing is displayed. The cursor M can be moved beyond the main window 31. Moreover, the cursor M is movable beyond a range of the main window 31. When an operator moves the cursor M by the mouse and presses down, for example, a left button mounted on the mouse, that is, clicks on the left button, the accepting section 13a accepts the input for providing an instruction to an object specified by the cursor M. Also, the accepting section 13a accepts the input for providing an instruction for pressing down each of the buttons 32 to 41 on the main window 31.

Figure 4:
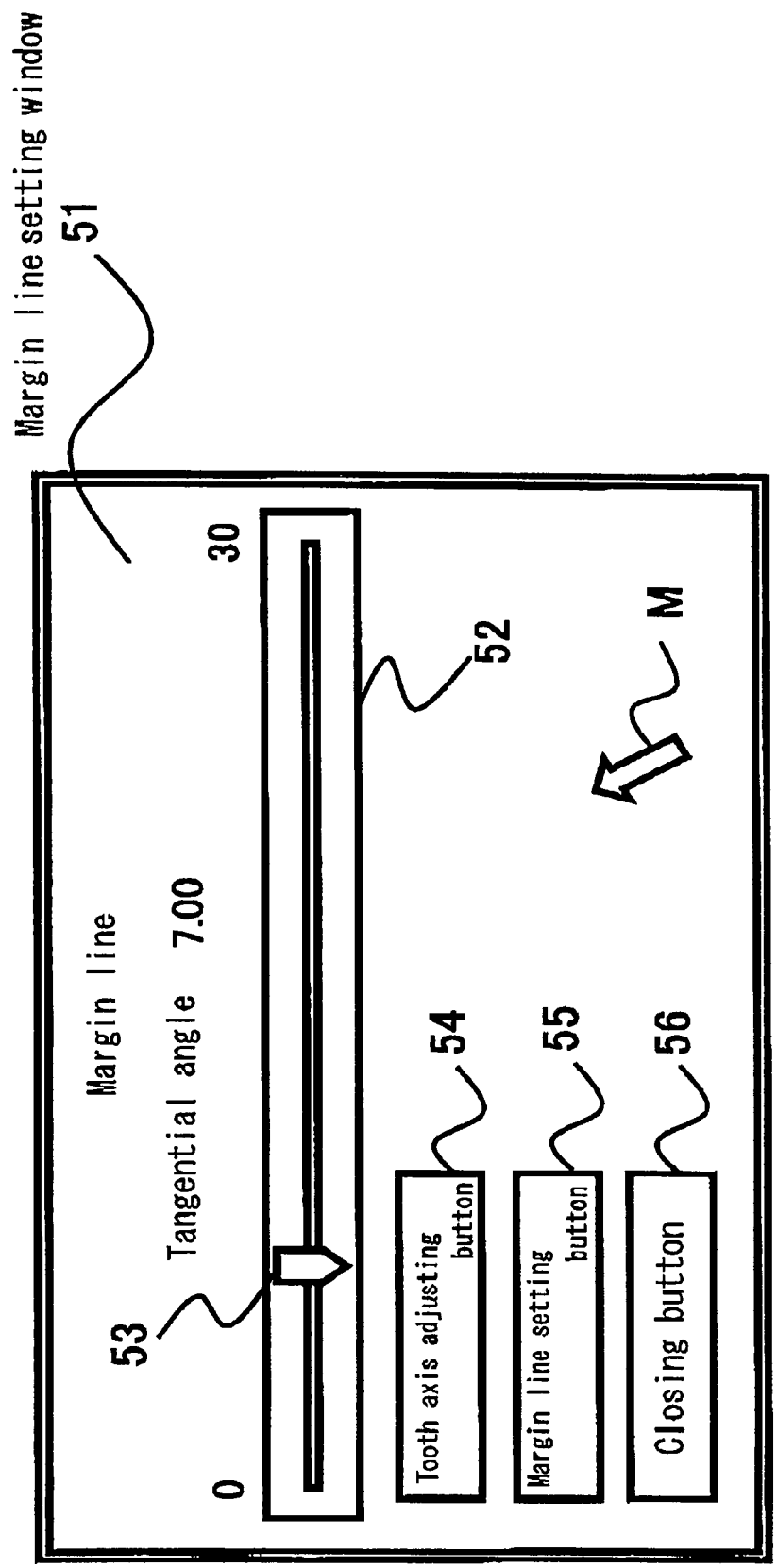
FIG. 4 is a diagram showing a margin line setting window according to the embodiment of the present invention.

FIG. 4 is a diagram showing a margin line setting window of the embodiment of the present invention. On the margin line setting window 51 are displayed a slide bar 52, a tooth axis adjusting button 54, a margin line setting button 55, a closing button 56. The slide bar 52 has a slidable knob 53 and accepts the specification of an angle formed between a line (tangential line) defining a contact point to be used at time of setting a margin line by using the slidable knob 53 and a reference axis Z. The tooth axis adjusting button 54 is a button to accept an instruction for adjusting the reference axis Z of a model to be processed. The margin line setting button 55 is a button to accept an instruction for setting a margin line by using the contact point defined by the tangential line whose angle is specified on the slide bar 52. The closing button 56 is a button to accept an instruction for terminating the processing of setting the margin line. Pressing down the closing button 56 causes the display controlling section 13b to close the margin line setting window 51.

On the margin line setting window 51, when the cursor M is moved by a mouse and the left button mounted on the mouse is clicked on by an operator, the accepting section 13a accepts the pressing-down of each of the buttons 54, 55, and 56. Also, when the cursor M is moved above the slidable knob 53 and is also moved left and right with the left button of the mouse being pressed down by the operator and an operation (dragging) of terminating a pressed-down state is performed, the accepting section 13a accepts the input of a tangential angle corresponding to a position of the slidable knob 53 as the designation of a new tangential angle.

Figure 5:
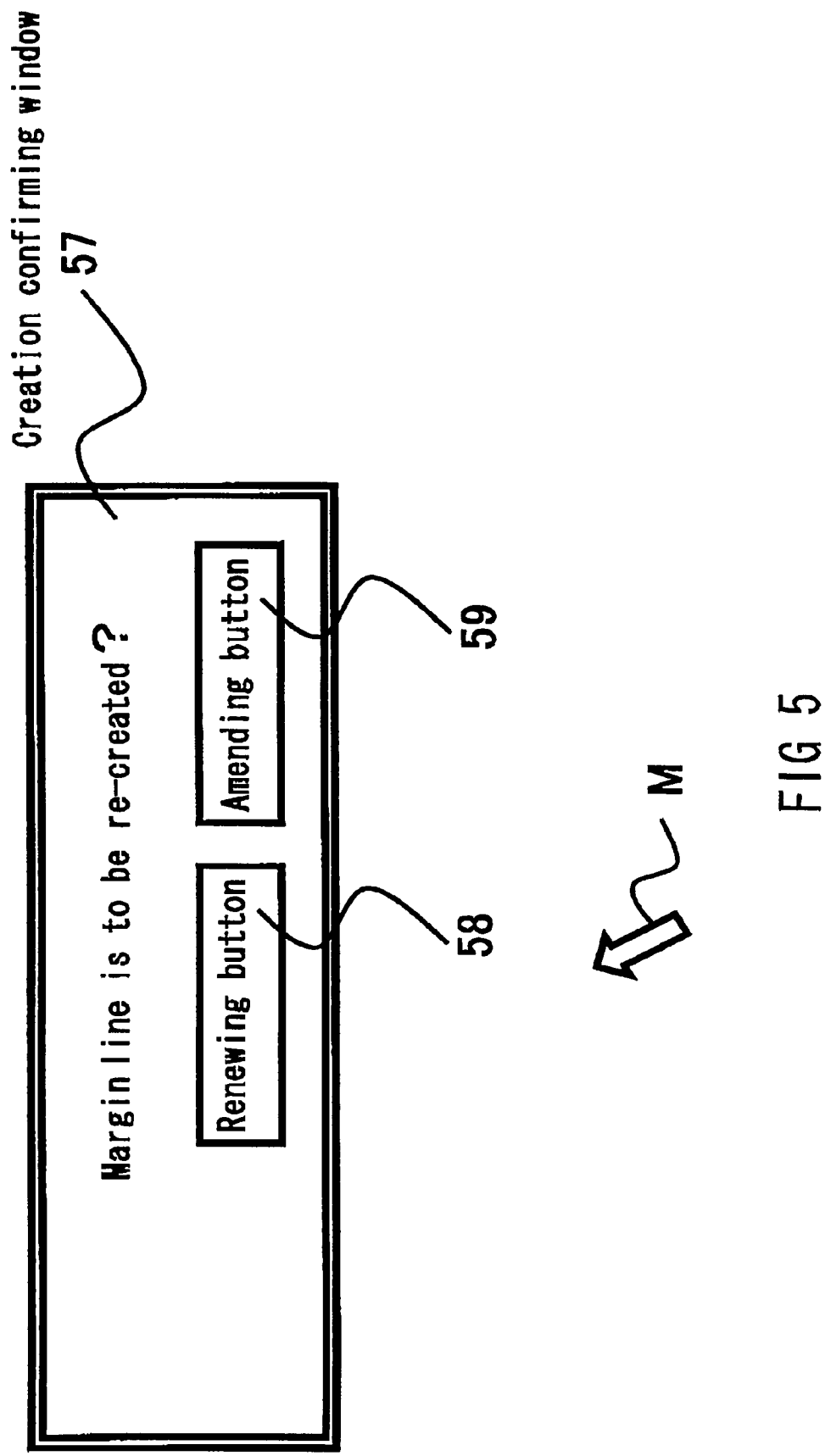
FIG. 5 is a diagram showing a creation confirming window according to the embodiment of the present invention.

FIG. 5 is a diagram showing a creation confirming window of the embodiment of the present invention. The creation confirming window 57 is a window to be displayed when the margin line setting button 55 is pressed down in the margin line setting window 51 and has a renewing button 58 and an amending button 59. The renewing button 58 is a button to accept an instruction for newly setting a margin line. The amending button 59 is a button to accept an instruction for amending a margin line already set. In the creation confirming window 57, when the cursor M is moved by the mouse and the left button mounted in the mouse is clicked on by an operator, the accepting section 13a accepts the pressing-down of each of the buttons 58 and 59.

Figure 6:
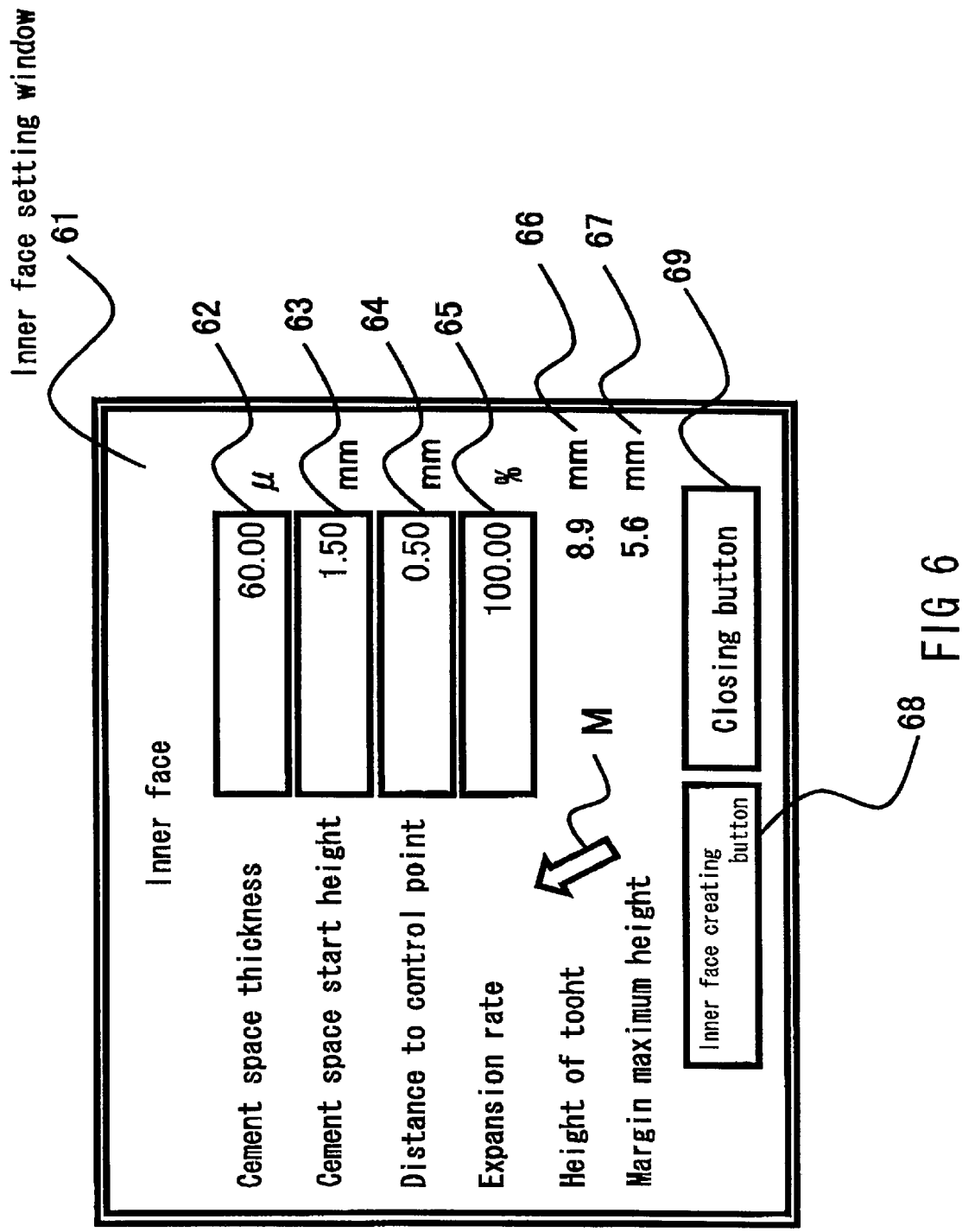
FIG. 6 is a diagram showing an inner face setting window according to the embodiment of the present invention.

FIG. 6 is a diagram showing an inner face setting window of the embodiment of the present invention. On the inner face setting window 61 are displayed a thickness inputting region 62 to which a thickness of cement space CST (see FIG. 7) is input, a start height inputting region 63 to which a height CSH (see FIG. 7) of the cement space CS is input, a control point distance region 64 to which a distance CD to a control point (see FIG. 7) is input, an zoom up rate inputting region 65 to which an zoom up rate of a volume of a coping C including the cement space CS is input, a tooth height display region 66 to which a height of a tooth (height of a model) in a direction from a specified reference face being vertical to the reference axis Z to a reference axis is displayed, a maximum height display region 67 in which a maximum height of a margin line in a direction from a specified reference face being vertical to the reference axis Z to a reference axis is displayed, an inner face creating button 68 and a closing button 69. According to the embodiment, only a value being smaller than a difference between a height of a tooth and a maximum height of a margin line is allowed to be set in the start height input region 63 and in the control point distance region 64.

The inner face creating button 68 is a button to accept an instruction for creating an inner face according to conditions set by the inner face setting window 61. The closing button 69 is a button to accept an instruction for terminating processing of inner face creation. When the closing button 69 is pressed down, the inner face setting window 61 is closed by the display controlling section 13b. In the inner face setting window 61, when the cursor M is moved by the mouse and the left button mounted on the mouse is clicked on by an operator, the accepting section 13a accepts the pressing-down of each of the buttons 68 and 69. Moreover, after the cursor M is moved into the input regions 62 to 65 and an operator clicks thereon, if a key of a keyboard being one example of the input device 12 is pressed down, the accepting section 13a accepts the input of characters input to a corresponding input region.

Figure 7:
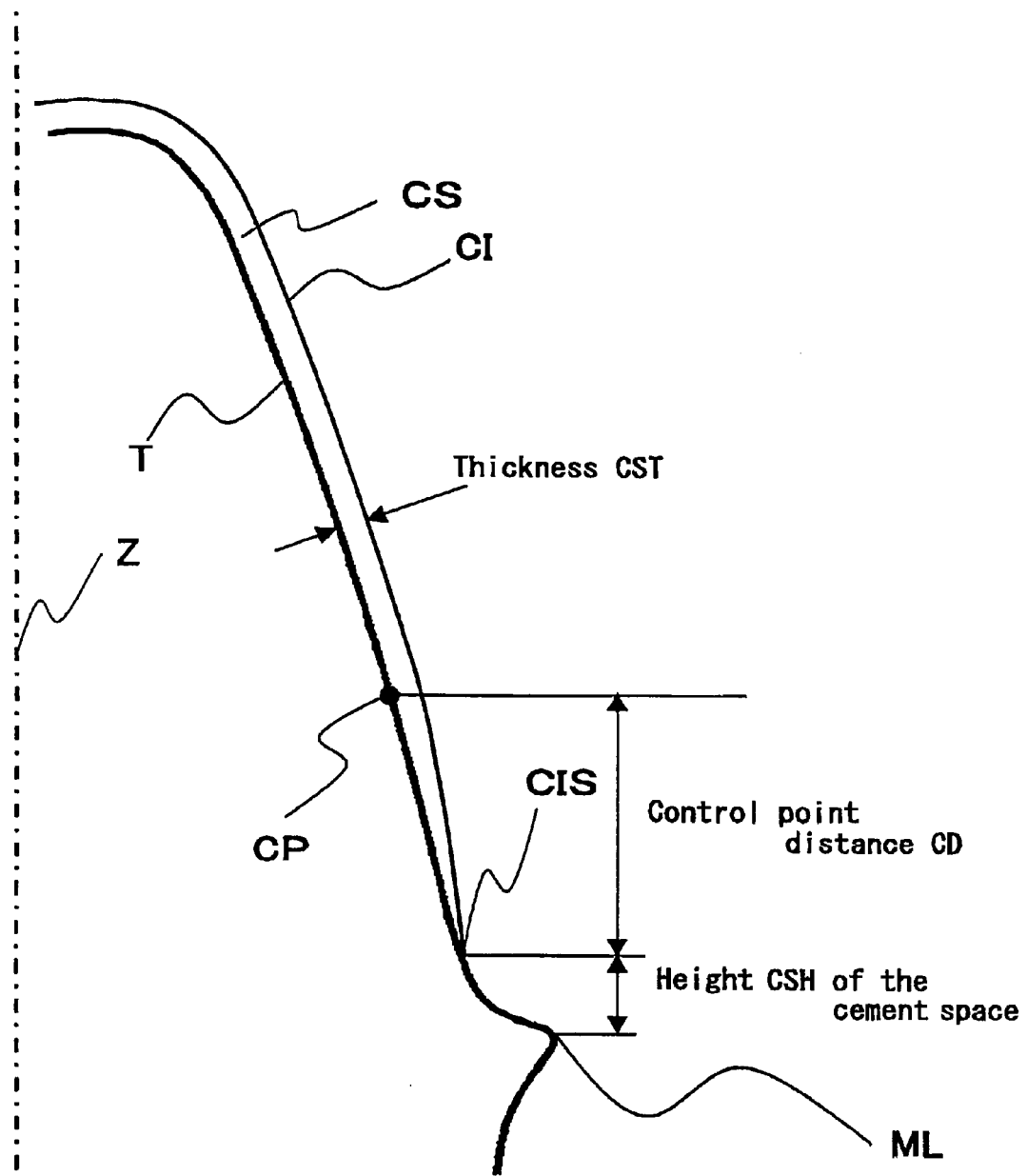
FIG. 7 is a diagram explaining setting conditions or a like for inner face setting according to the embodiment of the present invention.

Here, setting conditions or a like for the inner setting window 61 are described by referring to FIG. 7. FIG. 7 is a diagram explaining setting conditions or a like for inner face setting of the embodiment of the present invention. The thickness CST of the cement space CS, as shown in FIG. 7, refers to the maximum thickness in a region (cement space) (in an actual application, it is a region into which cement is put when a coping is adhesive, in a contacted manner, to an abutment tooth) between an abutment tooth model T and a coping inner face CI. The height CSH of the cement space CS, as shown in FIG. 7, refers to a height in a direction of a reference axis Z from a margin line ML to a starting position CIS from which the cement space CS starts. Moreover, the control point CP, as shown in FIG. 7, refers to a point at which the cement space CS becomes the thickness CST. Furthermore, the control point distance CD, as shown in FIG. 7, refers to a height in the reference axis Z direction from the starting position CIS from which the cement space CS starts to the control point CP.

Figure 8:
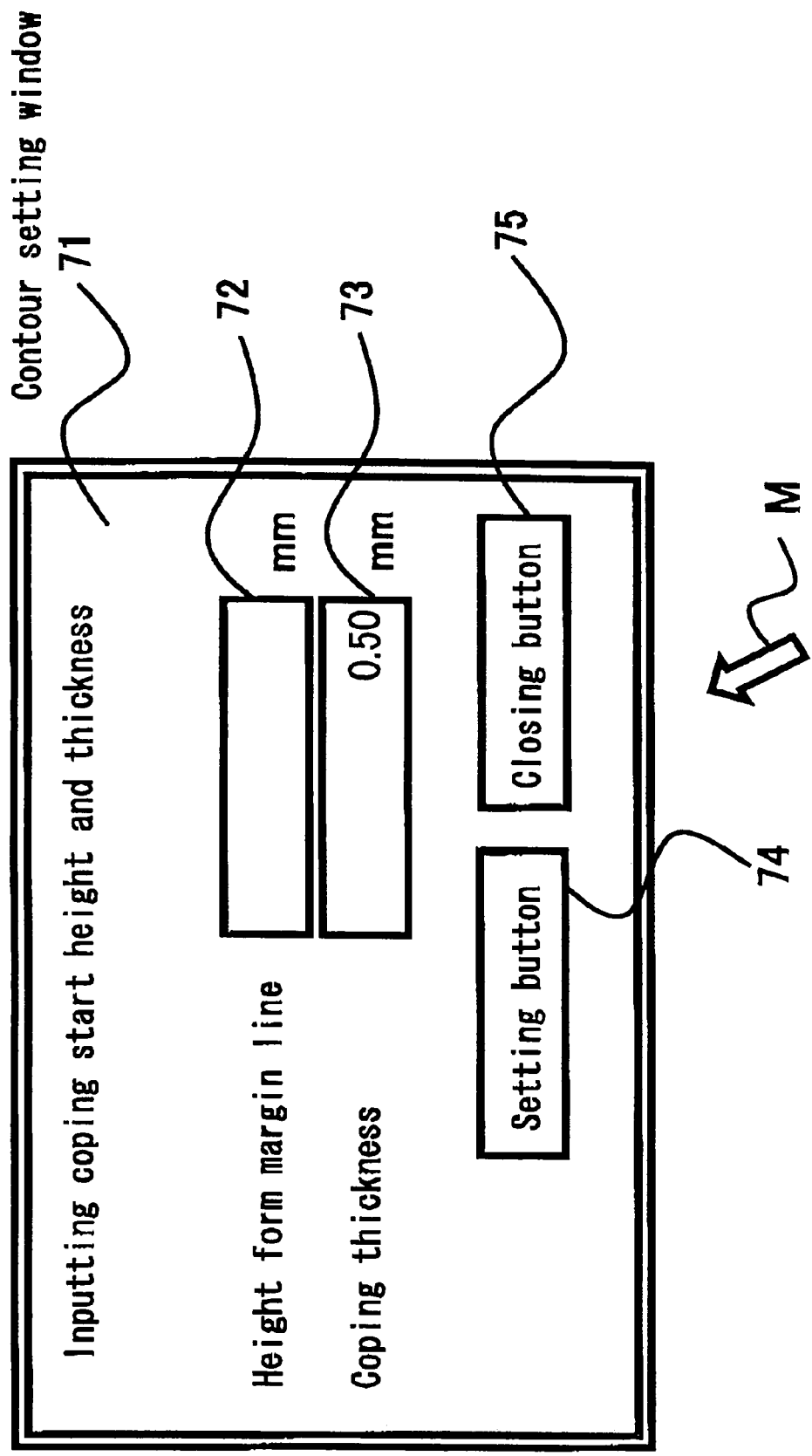
FIG. 8 is a diagram showing a contour setting window according to the embodiment of the present invention.

FIG. 8 is a diagram showing a contour setting window of the embodiment of the present invention. In the contour setting window 71 are displayed a height inputting region 72 in which a height COH (see FIG. 9) from the margin line ML is input, a coping thickness inputting region 73 in which a thickness CT of the coping C is input, a setting button 74, and a closing button 75. The setting button 74 is a button to accept an instruction for creating a contour according to conditions set by the contour setting window 71. The closing button 75 is a button to accept an instruction for terminating processing of creating a contour. When the closing button 75 is pressed down, the contour setting window 71 is closed by the display controlling section 13b.

In the contour setting window 71, when the cursor M is moved by the mouse and a left button mounted on the mouse is clicked on by an operator, the accepting section 13a accepts the pressing-down of each of the buttons 74 and 75. Besides, after the cursor M is moved above the inputting regions 72 and 73 and clicking by an operator is performed, if a key of the keyboard being an example of the input device 12 is pressed down, the accepting section 13a accepts the input of characters into the corresponding inputting region.

Figure 9:
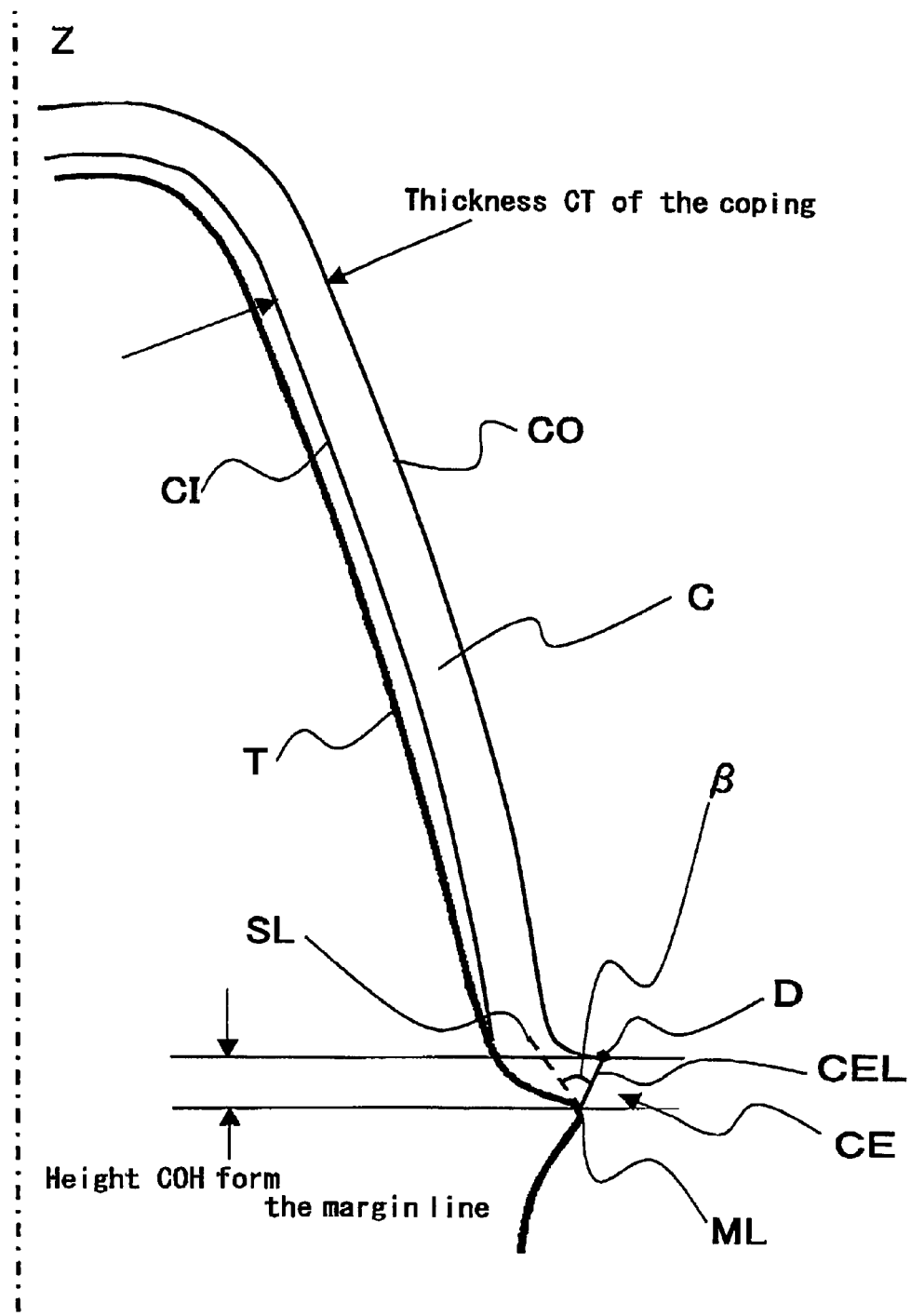
FIG. 9 is a diagram explaining setting conditions for setting an inner face according to the embodiment of the present invention.

Setting conditions or a like to be input in the contour setting window 71 are described by referring to FIG. 9. FIG. 9 is a diagram explaining setting conditions for setting an inner face of the embodiment of the present invention. The height COH from the margin line ML, as shown in FIG. 9, refers to a height in a reference axis Z direction from a margin line ML at an end point D of an outer face CO of the coping. The thickness CT of the coping, as shown in FIG. 9, refers to a thickness between an inner face and outer face of the coping.

According to the embodiment of the present invention, for example, a thickness of the coping C is constant and a line CEL on a side face CE of the coping C forms a specified angle β (for example, 60°) with a line SL on a face making up a model T existing in the neighborhood of a margin line and once one height COH on one thickness CT of the coping C is determined, the other height COH or the other thickness CT is automatically determined. Therefore, in the contour setting window 71, the input of either of the height COH from the margin line ML or the thickness CT of the coping C is accepted, The angle β formed between the line CEL on the side face CE of the coping C and the line SL on the face making up the model T existing in the neighborhood of the margin line ML is not restricted to the angle 60° described above and can be set, in a given manner, so as to correspond to materials for the coping C and to influences or a like caused by vibration occurring at time of working using the milling apparatus 4. Preferably, the angle β is an acute angle to reduce an amount of work of the coping C by a dental technician after the fabrication using the milling apparatus 4.

Referring to FIG. 2, the contact point detecting section 13c performs adjusting processing of a reference axis Z according to the operator's instruction accepted by the accepting section 13a. According to the embodiment of the present invention, the contact point detecting section 13c, when no instruction is provided, performs processing of setting a margin line using the reference axis Z at time of measurement, while performing processing of setting the margin line using the reference axis Z obtained after the adjustment if an instruction for the adjustment is provided. Moreover, the contact point detecting section 13c, based on the operator's specification accepted by the accepting section 13a, detects a contact point in a contour portion of a model in a plane containing the reference axis Z. The margin line determining section 13d determines a margin line based on the contact point detected by the contact point detecting section 13c. In the embodiment of the present invention, a line obtained by smoothly connecting a plurality of detected contact points using a specified algorithm is determined as a margin line and three-dimensional position data on the margin line is produced.

The coping processing section 13e produces three-dimensional shape data on shapes containing that of the inner face CI and of the contour (outer face CO and side face CE) of the coping C based on the three-dimensional position data of the margin line and the operator's specification accepted by the accepting section 13a. The milling setting processing section 13f produces data for fabrication and makes the communication processing section 13g transmit the produced data for fabrication of the coping C using the milling apparatus 4, based on the shape of the coping and the operator's specification accepted by the accepting section 13a. The communication processing section 13g receives the three-dimensional shape data on a model of an abutment tooth from the three-dimensional measuring apparatus 2 via the external interface 20 and stores it onto the hard disk driver 16. Moreover, the communication processing section 11g transmits the produced data for fabrication via the external interface 21 to the milling apparatus 4.

Figure 10:
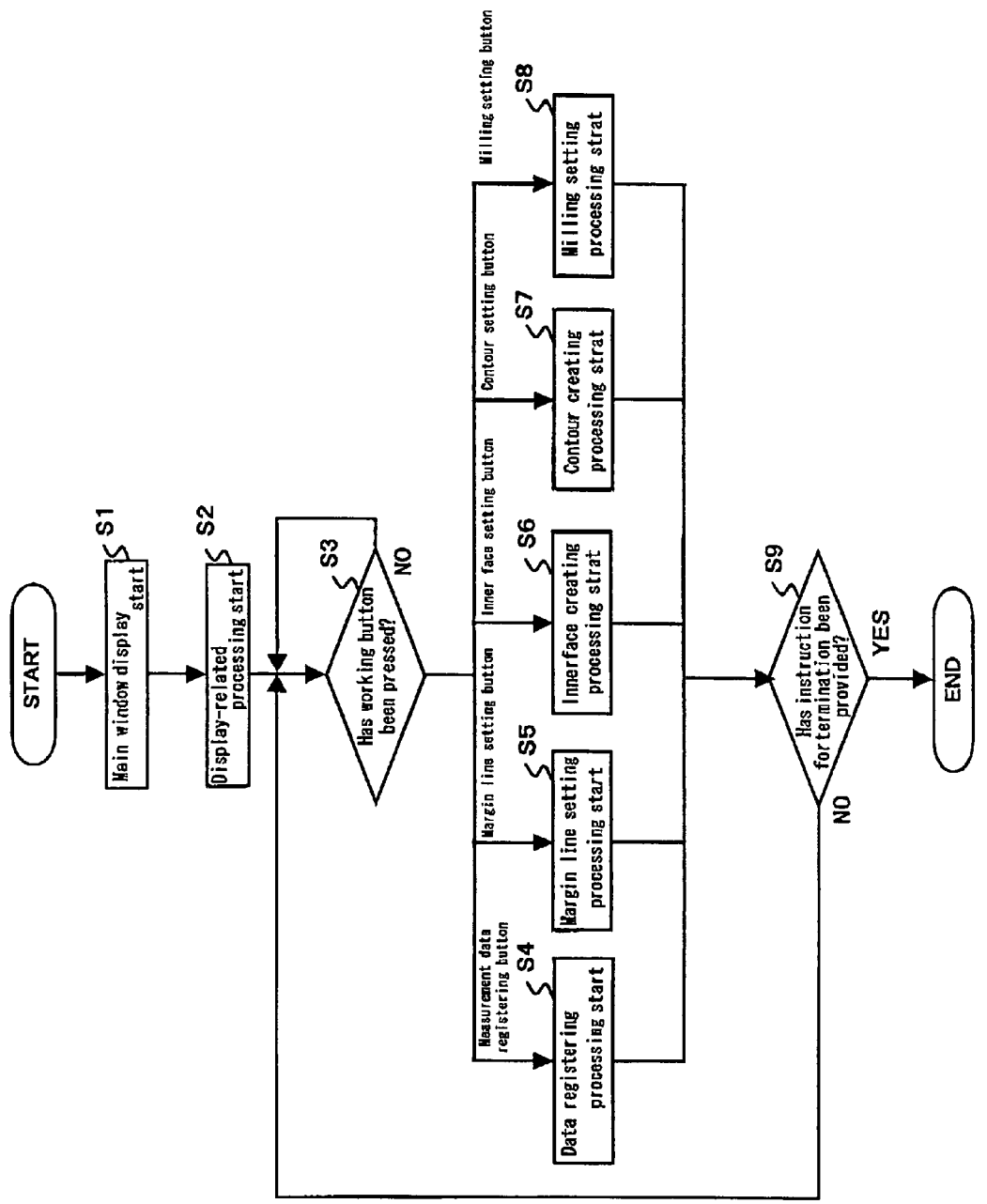
FIG. 10 is a flow chart explaining main processing according to the embodiment of the present invention.

Next, processing to be performed by the fabrication aiding apparatus according to the embodiment of the present invention is described. FIG. 10 is a flow chart explaining main processing of the embodiment. The main processing is started when starting-up of a fabrication aiding program is instructed by an operator's input device 12. At time of starting main processing, the display controlling section 13b makes the display processing section 17 display the main window 31 on the display device 11 (Step S1) and starts display-related processing (see FIG. 11) described later. Next, the accepting section 13a judges whether or not a specified working button has been pressed down on the main window 31 (Step S3) and, if the specified working button has not yet been pressed down, repeats the processing in the Step 3 and, if the button has been pressed down, processing according to the instruction provided by the pressed working button is started.

That is, when the accepting section 13a detects that the measurement data registering button 32 has been pressed down, data registering processing is started (Step S4). In the data registering processing, the display controlling section 13b displays a window on which the input of the specification of a file name of three-dimensional shape data of an abutment tooth model to be processed is accepted and the accepting section 13a accepts the operator's input operation on the window. Next, the display controlling section 13b acquires three-dimensional shape data having a file name accepted by the accepting section 13a from the hard disk driver 16 and have the data stored to the RAM 15 and displays a stereoscopic image in the image display region 37 based on the three-dimensional shape data.

Moreover, when the accepting section 13a detects that the margin line setting button 33 has been pressed down, margin line setting processing (see FIG. 12) described later is started (Step S5). Also, when the accepting section 13a detects that the inner face setting button 34 has been pressed down, inner face creating processing described later (see FIG. 16) is started (Step S6). Further, when the accepting section 13a detects that the contour setting button 35 has been pressed down, contour creating processing (see FIG. 17) described later is started (Step S7).

When the accepting section 13a detects that the milling setting processing button 36 has been pressed down, milling setting processing is started (Step S8). The milling setting processing is performed on a model whose contour creating processing has been performed and whose coping three-dimensional shape data has been performed. In the working processing, the milling setting processing section 13f accepts the input of setting contents of milling including the information about materials for a coping to be used at time of milling or about the setting of a rest to support a coping at time of working via the accepting section 13a from an operator and, based on the accepted set contents and the three-dimensional shape data on the coping C, produces data to be used for fabrication and makes the communication processing section 13g transmit the data for fabrication via the external interface 21 to the milling apparatus 4.

Then, after any of the processes (Steps S4, S5, S6, S7, and S8) is started, the accepting section 13a judges whether or not an instruction for termination has been provided, that is, whether or not the closing button 41 has been pressed down (Step S9) and, when the instruction for termination has been provided, the processing is terminated, while, no instruction is provided, the steps from the Step S3 are performed repeatedly.

Figure 11:
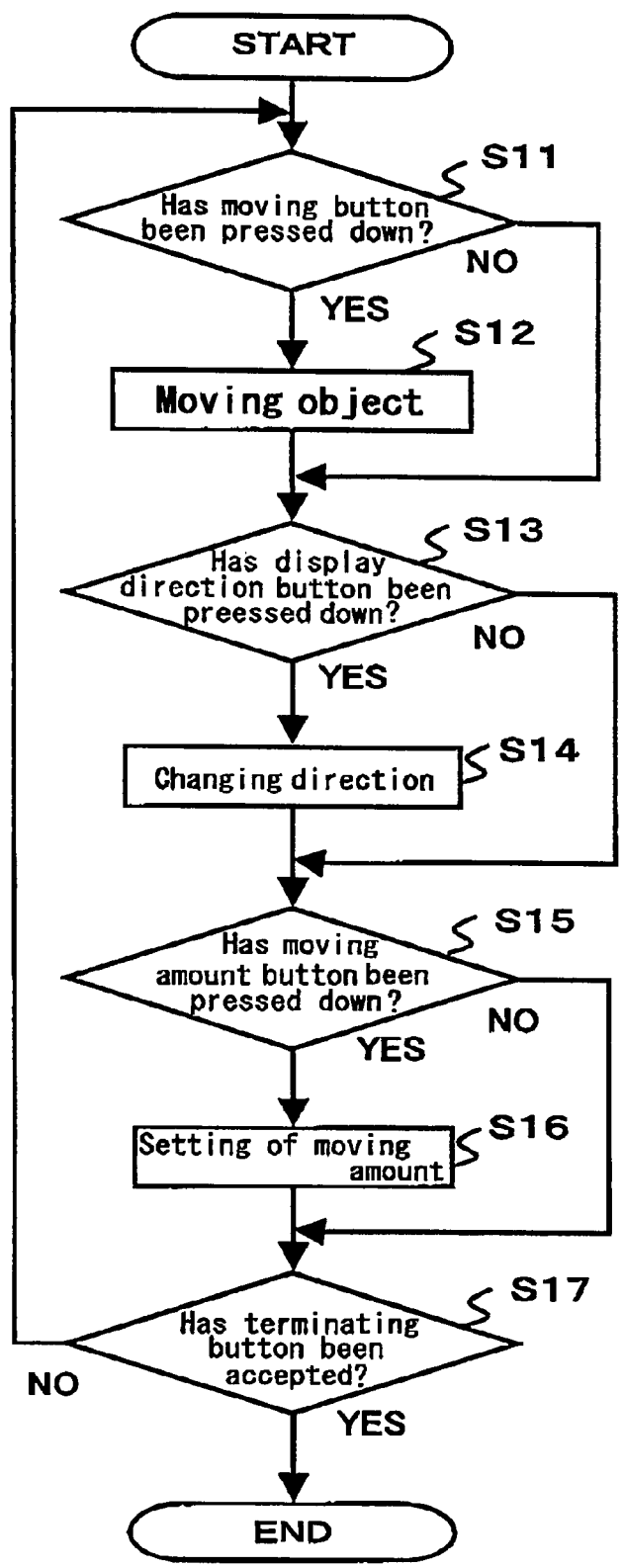
FIG. 11 is a flow chart explaining display-related processing according to the embodiment of the present invention.

Next, display related processing to be started in the Step S2 is described below. FIG. 11 is a flow chart explaining display-related processing of the embodiment of the present invention. In the display-related processing, the display controlling section 13b judges whether or not the accepting section 13a has accepted the pressing-down of any one of the image moving buttons 38 (Step S11) and, if the accepting section 13a has accepted, the display controlling section 13b moves an image of the model T displayed on the image display region 37 according to instructions provided by the pressed-down button (Step S12) and, if the accepting section 13a has not been accepted, performs nothing. Next, the display controlling section 13b judges whether or not pressing-down of any one of the buttons making up the image display direction button 39 has been accepted by the accepting section 13a

(Step S13) and, if the pressing-down has been accepted, according to an instruction provided by the pressed-down button, a front of an image of the model T being displayed on the image display region 37 is changed direction or an image being displayed is expanded or compressed (Step S14), while, if not, performs nothing.

Then, the display controlling section 13b judges whether or not pressing-down of any one of buttons making up the moving amount button 40 has been accepted by the accepting section 13a (Step S15) and, if the pressing-down has been accepted, sets a unit for a moving amount by using the image moving button 38 and image display direction button 39 according to an instruction provided by the pressed-down button (Step S16), and, if not, performs nothing. Then, the display controlling section 13b judges whether or not an instruction for termination has been accepted, that is, whether or not the closing button 41 has been pressed down (Step S17) and if the instruction for termination has been provided, terminates display-related processing, while, if not, repeats steps from the Step S11.

Figure 12:
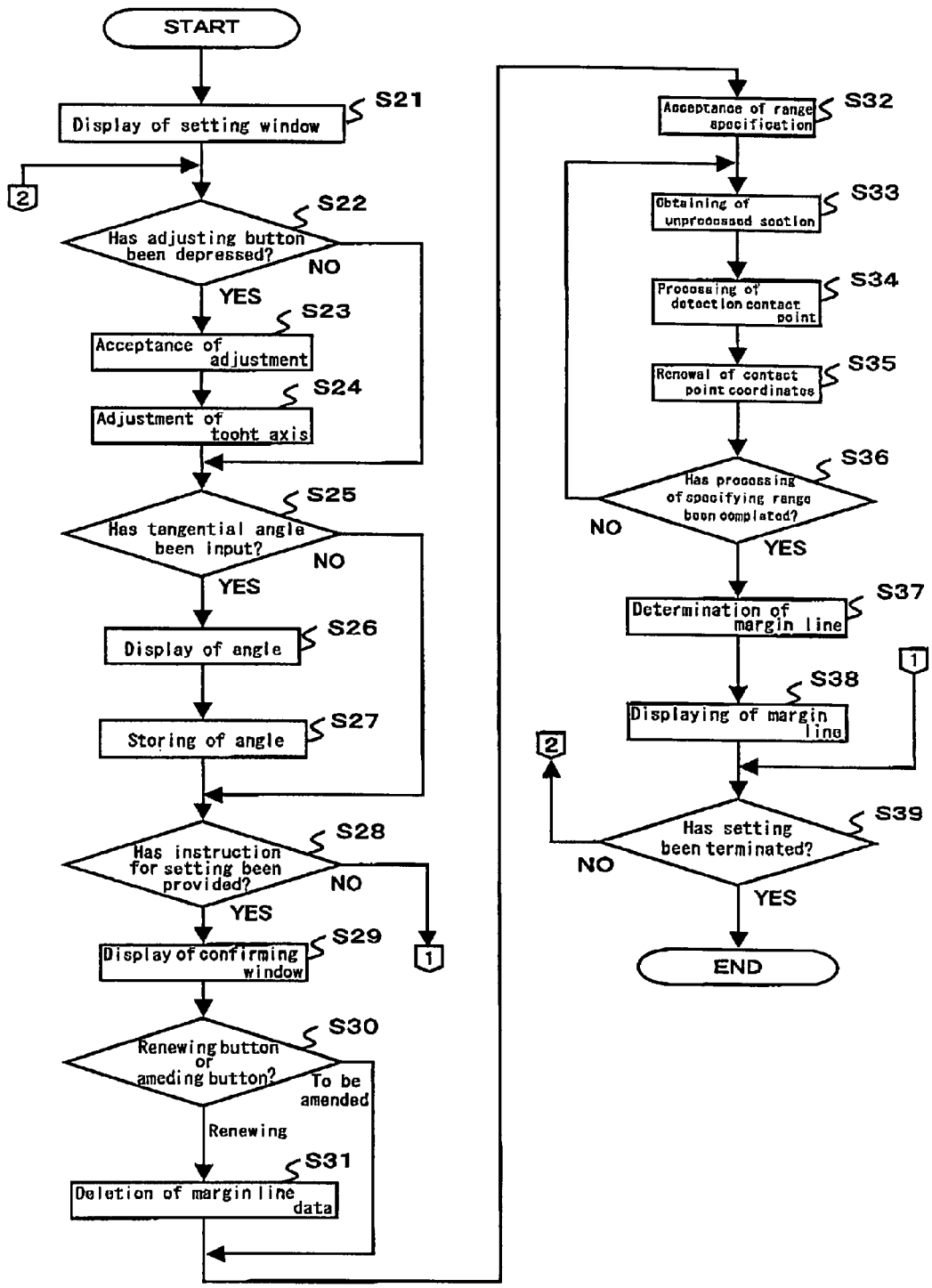
FIG. 12 is a flow chart explaining margin line setting processing according to the embodiment of the present invention.

Next, margin line setting processing in Step S5 is described below. FIG. 12 is a flow chart explaining margin line setting processing of the embodiment of the present invention. The margin line setting processing is performed in a state in which processing of registering data for measurement has been already performed and three-dimensional shape data on a model to be processed has been read to the RAM 15 and further an image of a corresponding model T has been displayed on the image display region 37. When the margin line setting processing is started, the display controlling section 13b makes the display processing section 17 display the setting window 51 on the display device 11 (Step S21). Next, the contact point detecting section 13c judges whether or not pressing-down of the tooth axis adjusting button 54 has been accepted by the accepting section 13a (Step S22) and, if the pressing-down has been accepted, adjusting operation of a reference axis (tooth axis) to be performed by the input device 12 from an operator is accepted by the accepting section 13a (Step S23). Here, examples of the adjusting operation of the reference axis include an operation of rotating an image of the model T displayed on the image display region 37 by using the mouse. Then, the contact point detecting section 13c performs processing of adjusting a tooth axis according to the adjusting operations (Step S24). More specifically, the reference axis specified by operations is used as a new reference axis and the three-dimensional shape data is adjusted so as to be used for a coordinate system in the new reference axis. Next, the contact point detecting section 13c judges whether or not operations of sliding the knob 53 of the slide bar 52 have been accepted by the accepting section 13a (Step S25) and, if the operations have been accepted, the display controlling section 13b changes a display of a tangential angle of the margin setting window 51 according to the sliding operations (Step S26) and stores the angle to the RAM 15 (Step S27).

Then, the contact point detecting section 13c judges whether or not pressing-down of the margin line setting button 55 has been accepted by the accepting section 13a (Step S28). If the pressing-down has not been accepted, the procedure proceeds to Step S39. On the other hand, if the pressing-down has been accepted, the display controlling section 13b displays the creation confirming window 57 on the display device 11 (Step S29). Next, the contact point detecting section 13c judges whether or not pressing-down of either of the renewing button 58 or amending button 59 has been accepted (Step S30) and, if the pressing-down of the renewing button 59 has been accepted, deletes the three-dimensional shape data stored in the RAM 15 (Step S31) and, if the pressing-down of the amending button 59 has been accepted, the three-dimensional shape data of the margin line already obtained remains left as it is.

Next, the accepting section 13a accepts the specification of a range in the reference axis Z in which a contact point should be detected and the specification of a detecting range in a direction surrounding the reference axis Z (Step S32). Then, the contact point detecting section 13c obtains coordinates of a plurality of points, existing in the direction of the reference axis Z, in a cross section containing the reference axis Z of the model T that is within a detecting range in a direction surrounding the reference axis Z and in which processing of detecting a contact point is not performed. Here, the points at which coordinates are to be obtained may be points that can be directly obtained at time of measurement or points existing among measured points that can be obtained by a specified calculation based on the measured points. The points among measured points may appear on, for example, a Be'zier curve. Next, contact point detecting processing of detecting a contact point form the plurality of contact points (Step S34) and three-dimensional coordinates (three-dimensional position information) of a contact point in the cross section of the model T are written to the RAM 15 as the coordinates newly detected (Step S35). As a result, at time of amending the margin line, coordinates of a contact point before the amendment are renewed to be coordinates of the contact point in a corresponding cross section with respect to lines having a newly specified angle.

Then, the contact point detecting section 13c Judges whether or not processing has been performed on all cross sections in which a contact point is to be detected in the direction surrounding the reference axis being within the detecting range (Step S36). If the processing has not been performed, the procedure returns to Step S33. On the other hand, when the processing has been performed (YES in the Step S36), three-dimensional shape data (three-dimensional position information) of the margin line in the model is determined (Step S37) based on coordinates of a plurality of contact points being stored in the RAM 15. Here, the margin line is determined, for example, as three-dimensional shape data for smoothly connecting the plurality of contact points.

Next, based on the three-dimensional shape data determined by the display controlling section 13b, a margin line is displayed on an image of the model T being displayed in the image display region 37 (Step S38). Then, the margin line determining section 13d judges whether or not the accepting section 13a has been pressed down (Step S39) and, if the instruction for termination has been provided, terminates the margin line setting processing, while, if no instruction has been provided, the steps from the Step S22 are repeated.

Figure 13:
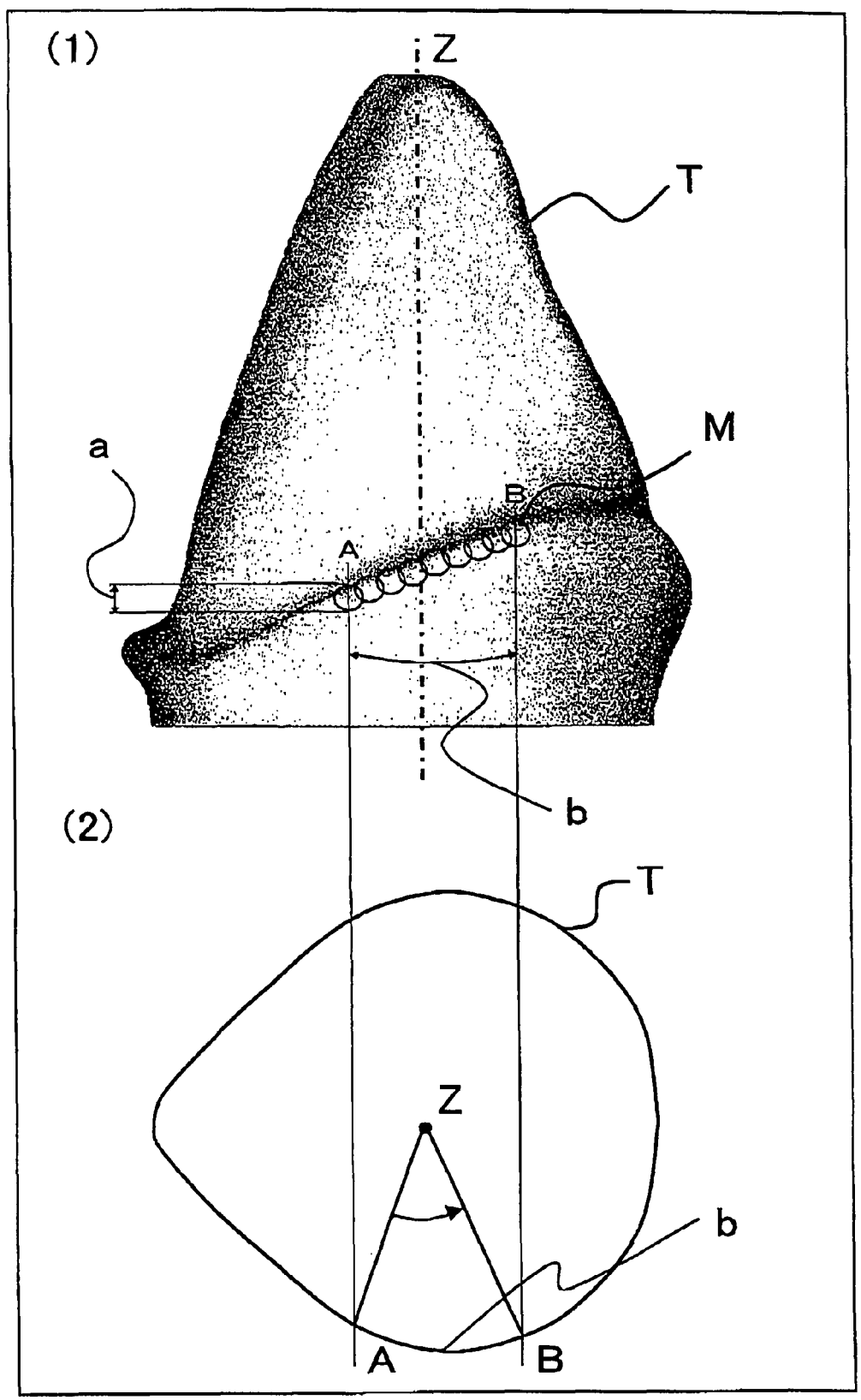
FIG. 13 is a diagram explaining the specification of a detecting range of a margin line according to the embodiment of the present invention.

Next, specification of a detecting range in the Step S32 is described in detail by using FIG. 13. FIG. 13 is a diagram explaining the specification of a detecting range of a margin line of the embodiment of the present invention. FIG. 13 (1) is an explanatory diagram using an example displayed in the image display region 37 of the main window 31 at time of specifying a detecting range and FIG. 1 (2) is a diagram explaining a detecting range in the case shown in FIG. 13 (1). As shown in FIG. 13 (1), in the image display region 37 on the main window 31, the model T of an abutment tooth is stereoscopically displayed. When a detecting range is specified, the cursor M is of a circular shape as shown in FIG. 13 (1). According to the embodiment, the accepting section 13a accepts the specification of a detecting range in which a contact point is detected by an operation (dragging operation)

in which the cursor M is moved with a left button of the mouse, which is one example of the input device 12, being pressed.

The width "a" of the cursor M in a direction of the reference axis Z at each position through which the cursor M passed at time of a dragging operation shows a range of a point in a circumference at which a contact point should be detected in a cross section containing the point in the circumference of the model T indicated by a central point of the cursor M at each position and the reference axis Z. Moreover, a range in a direction surrounding the reference axis Z defined when the dragging operation was performed, for example, a range "b" from a position A to a position B shown in FIG. 13 (1), shows a range in a direction surrounding the reference axis Z in which a contact point should be detected. When the range from the position A to the position B shown in FIG. 13 (1) is specified, as shown in FIG. 13 (2), it means that a contact point in each cross section containing the reference axis Z should be detected in the range "b" from a circumferential portion indicated by the position A of the model T to a circumferential portion indicated by the position B of the model T.

Figure 14:
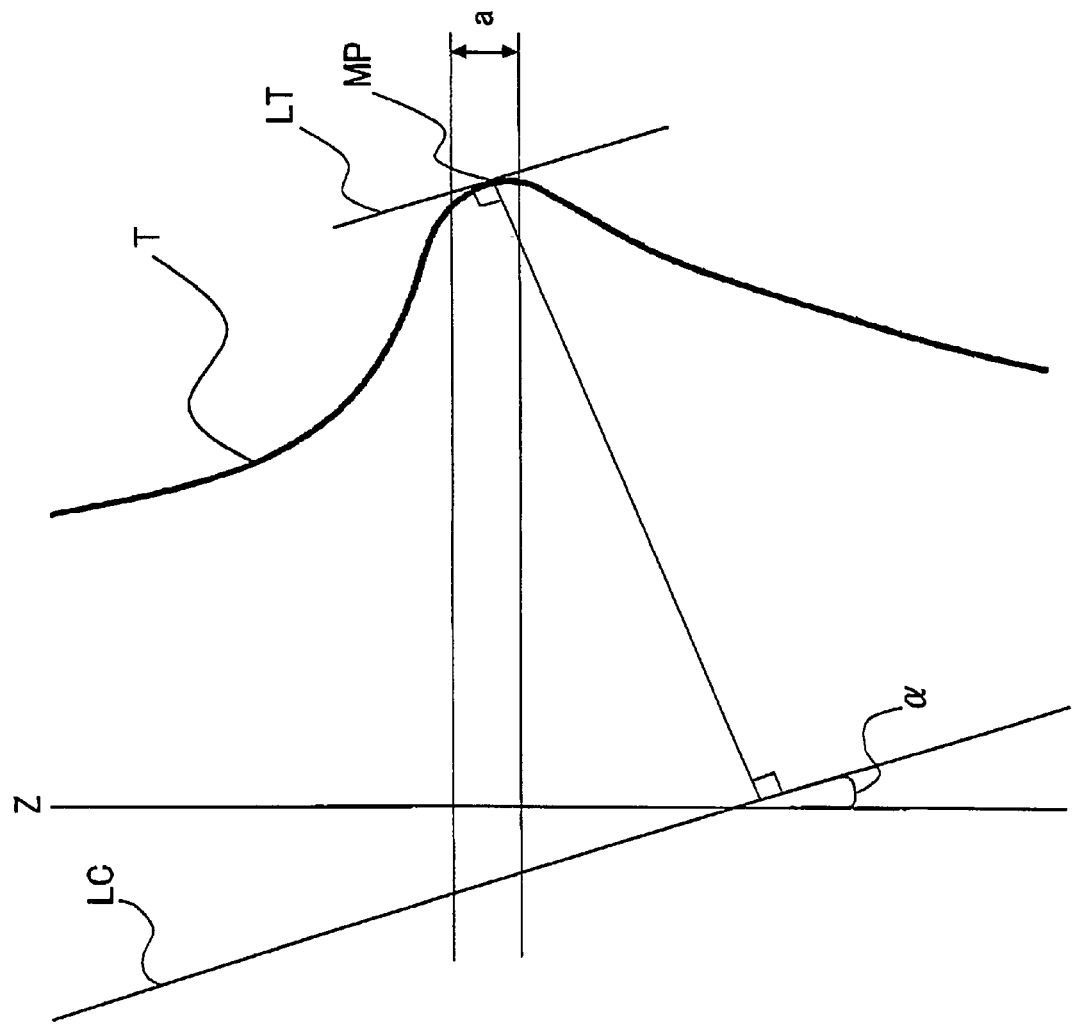
FIG. 14 is a diagram explaining processing of detecting a contact point of a margin line according to the embodiment of the present invention.

Next, the contact point detecting processing in Step S34 is described in detail by using FIG. 14. FIG. 14 is a diagram explaining the processing of detecting a contact point of a margin line of the embodiment of the present invention. FIG. 14 also shows one example of a cross section containing the reference axis Z in a detecting range in a direction surrounding the reference axis Z. In the contact point detecting processing, the contact point detecting section 13c detects a contact point MP in a circumferential portion of the model T being in contact with a line LT having a specified angle (in FIG. 14, the angle "α") formed with the reference axis Z. According to the embodiment, the contact point detecting section 13c is configured to first detect a line LC to be used for calculation which is positioned on a side of the model T being much inner than a circumferential portion within a detecting range "a" in the reference axis direction and has a specified angle "α" formed with the reference axis Z. The line LC for calculation forming a specified angle "α" with the Z axis and having an intercept positioned lower than Z axis coordinates that occupy the lowest portion of the detecting range "a" in a direction of the reference axis can be used. Then, the contact point detecting section 13c obtains a plurality of points existing in a circumferential portion of the model T within the detecting range "a" and calculates a distance between each of the plurality of points and the line LC for calculation. The contact point detecting section 13c determines the farthest point from the plurality of points as a contact point. According to the embodiment, only a point within a limited detecting range in the direction of the reference axis is used for the detection of the contact point and, therefore, it is made possible to detect a contact point with a small amount of processing. Additionally, since a contact point can be detected by calculating only a distance from the line for calculation, no complicated calculation is required.

Figure 15:
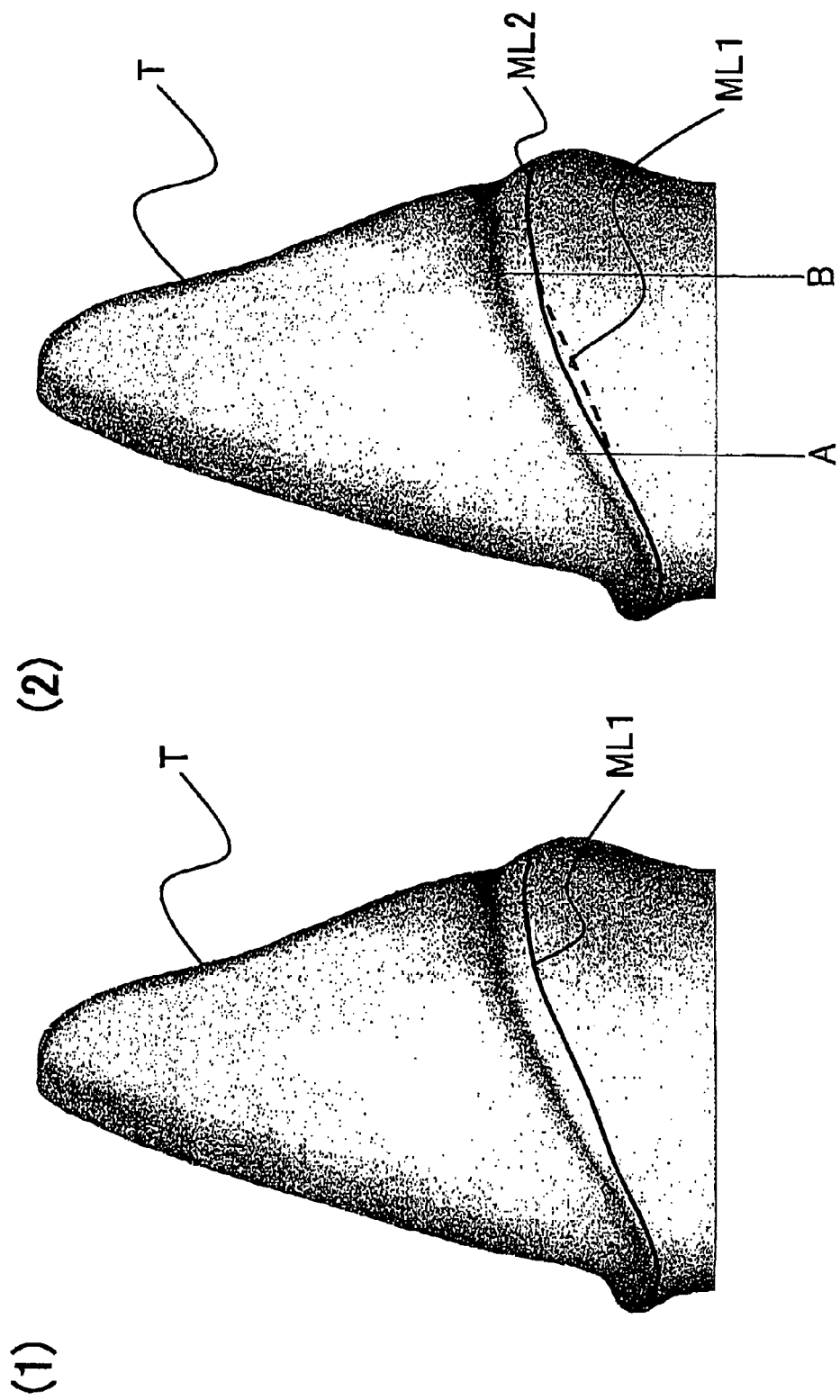
FIG. 15 is a diagram explaining a detected margin line according to the embodiment of the present invention.

Next, a margin line set by the margin line setting processing is described by using FIG. 15. FIG. 15 is a diagram explaining a detected margin line of the embodiment. For example, after one tangential angle is specified by using the margin line setting window 51 and, after the margin line setting button 55 is pressed down, when the cursor M is moved, by a dragging operation, over all circumferences in a range in which margin lines of the model T exist, as shown in FIG. 15 (1), a contact point in each cross section in a direction surrounding the reference axis Z is detected and the margin line ML1 obtained by smoothly connecting each point is displayed with the margin line ML1 being superimposed on an image of the model T displayed in the image display region 37 on the main window 31.

Besides, thereafter, when, on the margin line setting window 51, for example, a tangential angle is specified so as to have a larger angle and the amending button 59 is pressed down on the creation confirming window 57 and further the cursor M is moved from the position A to the position B by the dragging operation of the mouse, a tangential line with a new angle is detected within a range from the position A to the position B and, as shown in FIG. 15 (2), a new margin line ML2 obtained by being replaced in the place from the position A to the position B is displayed. Thus, in the direction surrounding the reference axis Z of the model T, it is possible to easily set a margin line obtained by connecting contact points with lines each having a plurality of different angles. Therefore, by checking the margin line ML appearing on the image of the stereoscopic model T and by newly detecting contact points by using lines with new angles only in part of a range not being desirable for detection of a margin line in a direction surrounding the reference axis Z, a margin line can be easily reset.

Figure 16:
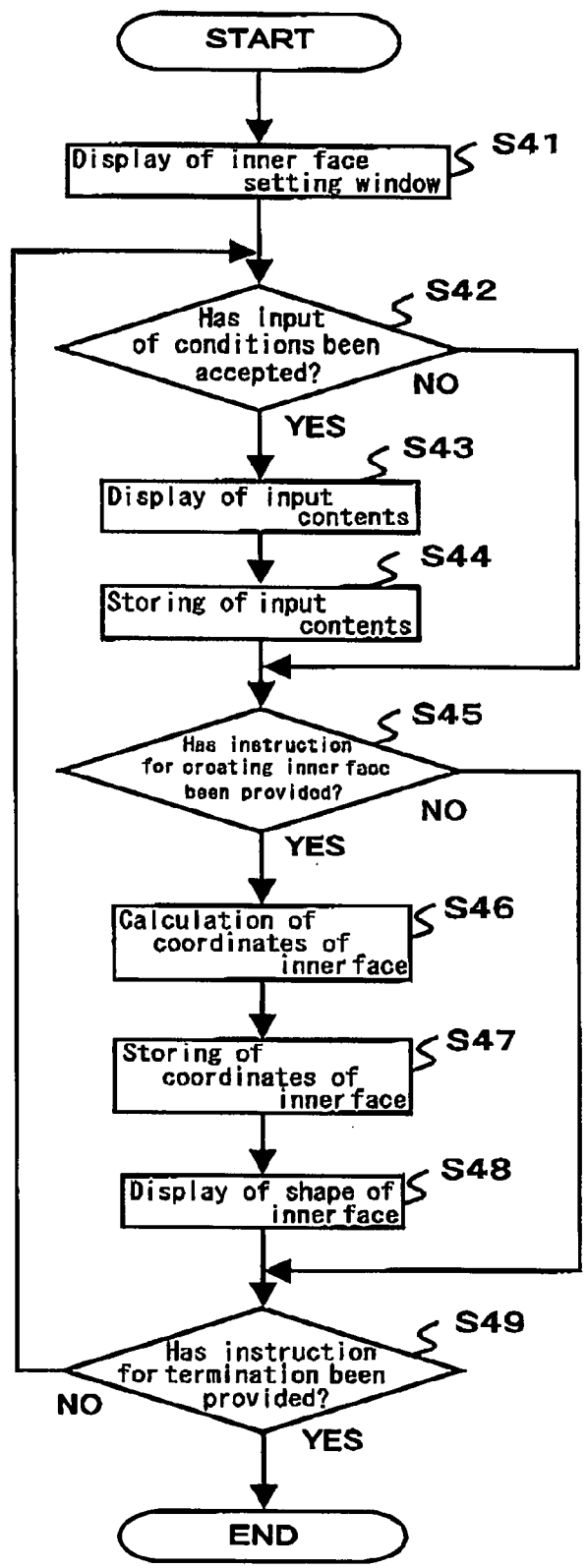
FIG. 16 is a flow chart explaining inner face creating processing according to the embodiment of the present invention.

Next, the inner face creating processing to be started in the Step S6 is described. FIG. 16 is a flow chart explaining the inner face creating processing of the embodiment of the present invention. The inner face creating processing is performed in a state in which the margin line setting processing has already been performed and three-dimensional shape data of a margin line of the model T has been created. When the inner face creating processing is started, the display controlling section 13b makes the display processing section 17 display the inner face setting window 61 on the display device 11 (Step S41). Moreover, in each of the input regions on the inner face setting window, for example, a set value for default or a like is displayed. Next, the coping processing section 13e judges whether or not the input of inner face setting conditions including a cement space thickness, height of cement space, distance to a controlling point, or a like has been accepted by the accepting section 13a and, if the input has been accepted, makes the display controlling section 13b display setting conditions on the inner face setting window (Step S43) and contents of the setting be stored to the RAM 15 (Step S44). If the input has not been accepted, nothing is performed.

Then, the coping processing section 13e judges whether or not pressing-down of the inner face creating button 68 has been accepted (Step S45) and, if the pressing-down has been accepted, calculates three-dimensional coordinates of the inner face of the coping based on the setting conditions of the coping processing section 13e (Step S46) and makes the coordinates be stored to the RAM 15 (Step S47). Also, the display controlling section 13b combines shapes of the coping inner face with the image of the model T and displays the combined image in the image display region 37 on the main window 31 (Step S48). Moreover, if the pressing-down of the inner face creating button 68 has not been accepted ("NO" in the Step S45), the processing proceeds to the next Step S49. Then, the coping processing section 13e judges whether or not an instruction for termination has been accepted by the accepting section 13a, that is, whether or not the pressing-down of the closing button 69 has been accepted (Step S49) and, if the instruction for termination has been provided, terminates the inner face creating processing, while, if no instruction has been provided, the steps from the Step S42 are performed repeatedly.

Figure 17:
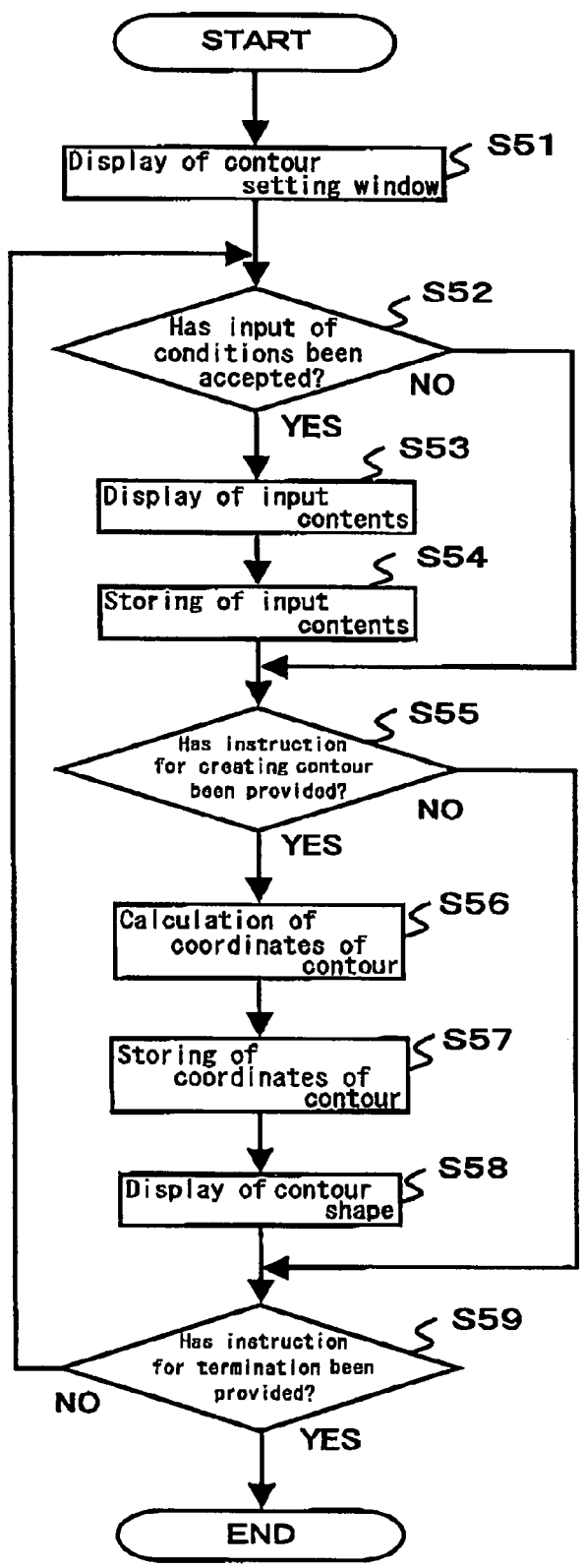
FIG. 17 is a flow chart explaining contour creating processing according to the embodiment of the present invention.

Next, the contour creating processing to be started in the Step S7 is described. FIG. 17 is a flow chart explaining contour creating processing of the embodiment of the present invention. The contour creating processing is performed in a state in which the inner face creating processing has been already performed and three-dimensional shape data on a margin line of the model T has been obtained and further coordinates of an inner face of the coping has been determined. When the contour creating processing is started, the display controlling section 13b makes the display processing section 17 display the contour setting window 71 on the display device 11 (Step S51). Moreover, in one of the contour setting window 71, for example, a set value of a default is displayed. Next, the coping processing section 13e judges whether or not the input of setting conditions of either of a height from a margin line or a thickness of the coping has been accepted by the accepting section 13a (Step 13b display setting conditions on the contour setting window 71 (Step S53) and contents of the setting be stored in the RAM 15. If the input has not been accepted, nothing is performed.

Then, the coping processing section 13e judges whether or not pressing-down of the setting button 74 has been accepted by the accepting section 74 (Step S55) and, if the pressing-down has been accepted, calculates three-dimensional coordinates of a shape of a contour (outer face CO and side face CE) of the coping C (Step S56) and makes the coordinates be stored in the RAM 15 (Step S57). Here, according to the embodiment, as shown in FIG. 9, three-dimensional coordinates (three-dimensional position information) of a shape of a side CE are detected in all the circumference of the reference axis Z so that a line CEL on the side CE of the coping C forms a specified angle (for example, 60°) with a face of the model T in the neighborhood of the margin line ML. More specifically, a face containing the reference axis Z is determined for every specified angle in a direction surrounding the reference axis Z and coordinates of the line CEL on a side face CE of the coping C are calculated, for every face, so that a specified angle β (for example, 60°) is formed between the margin line ML and the line SL being connected to a point of the model T in the neighborhood of the margin line ML. Then, the display controlling section 13b combines a shape of a contour of the coping C with the image of the model T and displays the combined image in the image display region 37 on the main window 31 (Step S58). Moreover, if the pressing-down of the setting button 74 has not been accepted ("NO" in the Step S55), the processing proceeds to the next Step S59.

Next, the coping processing section 18e judges whether or not an instruction for termination has been accepted by the accepting section 18a, that is, whether or not the pressing-down of the closing button 75 has been accepted (Step S59) and, if the instruction for termination has been provided, terminates the contour creating processing, while, if no instruction has been provided, the steps from the Step S42 are performed repeatedly As described above, in the embodiment, three-dimensional coordinates of a shape of a side face is detected so that the line CEL on the side face CE of the coping C forms a specified angle β with a face of the model T in the neighborhood of the margin line ML and, therefore, a specified angle is formed between an inner face and a side face of the actual coping C fabricated by the milling apparatus 4. As a result, it is made possible to effectively prevent breakage of the coping C due to vibration or a like at time of milling occurring in the middle of fabrication using the milling apparatus 4. Moreover, it is also made possible to reduce an amount of milling the side face CE of the coping C, that has to be performed manually by a dental technician, fabricated by the milling apparatus 4. Additionally, the angle formed between the inner face CI and side face CE of the coping C is a specified angle, it is made possible for a dental technician to easily obtain knowledge of a portion that has to be cut by the dental technician, by using the specified angle as a reference.

It is apparent that the present invention is not restricted to the above embodiments but may be changed and modified without departing from the scope and spirit of the invention. For example, in the above embodiment, whether or not a point in a circumferential portion of the model T is a contact point is judged by determining the line LC to be used for calculation and by using a distance form the line LC. However, the present invention is not restricted to this method. For example, a contact point may be detected by calculating a function of a line in a circumferential portion and by sequentially changing an intercept of a reference axis with respect to a function of a straight line having a specified angle and by using a relation among these functions. Also, in the above embodiment, a contact point is detected by using a line for calculation existing in a place being inner than a detecting range portion of the model T, however, the present invention is not restricted to this. That is, for example, a contact point may be detected by using a line for calculation existing in a place being outer than the detecting range portion of the model T. In this case, a point being nearest from a straight line can be used as a contact point.

Additionally, in the above embodiment, the fabrication aiding apparatus 3 is directly connected to the three-dimensional measuring apparatus 2 via a cable, however, this invention is not restricted to this. That is, these two apparatuses may be connected to each other via a communication network such as a LAN (Local Area Network), WAN (Wide Area Network), or a like. Furthermore, the fabrication aiding apparatus 3 and the milling apparatus 4 may be connected to each other via the network including a LAN, WAN, or a like.

What is claimed is:

1. A fabrication aiding apparatus, comprising:
shape data storing means to store three-dimensional shape data on a model of an abutment tooth to which a dental prosthesis is applied;
angle input accepting means to accept an input of specification of an angle;
contact point detecting means to detect, based on the three-dimensional shape data, three-dimensional position information about a contact point of said model with a line that is tangent with said model, and forms said angle with a reference axis on a face containing the reference axis; and
margin line determining means to determine, based on coordinates of the contact point, three-dimensional position information of a margin line in said model of said abutment tooth.

2. The fabrication aiding apparatus according to claim 1, further comprising detecting range input accepting means to accept an input of a detecting range in which the contact point with the line having the specified angle in said model of said abutment tooth is detected.

3. The fabrication aiding apparatus according to claim 2, further comprising display means to stereoscopically display said model on a display device based on the three-dimensional shape data, wherein said detecting range input accepting means accepts an input of specification of the detecting range according to a mark on said model stereoscopically displayed.

4. The fabrication aiding apparatus according to claim 2, wherein said detecting range input accepting means accepts an input of a detecting range in a direction of the reference axis.

5. The fabrication aiding apparatus according to claim 4, wherein said contact point detecting means detects a contact point by judging whether or not a plurality of points of said model that belong to a detecting range in the reference axis direction on a face containing the reference axis is a contact point with a tangential line having the angle.

6. The fabrication aiding apparatus according to claim 2, wherein said detecting range input accepting means accepts an input of a detecting range in a direction surrounding the reference axis.

7. The fabrication aiding apparatus according to claim 6, wherein said angle input accepting means accepts an input of specification of a plurality of angles, said detecting range input accepting means accepts an input of each of detecting ranges in the direction surrounding the reference axis in which a contact point with the line having each of specified angles is detected, said contact point detecting means detects, within each of the detecting range, a contact point with the line having each of the specified angles, and said margin line determining means determines three-dimensional position information about a margin line in the model of the abutment tooth based on the contact point detected within each of the detecting range.

8. The fabrication aiding apparatus according to claim 3, wherein said detecting range input accepting means accepts an input of a detecting range in a direction of the reference axis.

9. The fabrication aiding apparatus according to claim 3, wherein said detecting range input accepting means accepts an input of a detecting range in a direction surrounding the reference axis.

10. The fabrication aiding apparatus according to claim 4, wherein said detecting range input accepting means accepts an input of a detecting range in a direction surrounding the reference axis.

11. The fabrication aiding apparatus according to claim 5, wherein said detecting range input accepting means accepts an input of a detecting range in a direction surrounding the reference axis.

12. A fabrication aiding apparatus, comprising:
shape data storing means to store three-dimensional shape data on a model of an abutment tooth to which a dental prosthesis is applied;
angle input accepting means to accept an input of specification of an angle;
detecting range input accepting means to accept an input of a detecting range in a direction of a reference axis;
contact point detecting means to detect, based on the three-dimensional shape data three-dimensional position information about a contact point; and
margin line determining means to determine, based on coordinates of the contact point, three-dimensional position information of a margin line in said model of said abutment tooth,
wherein said contact point detecting means determines a line to be used for calculation that exists on a side of said model being inner than a plurality of points of said model that belongs to a detecting range in the direction of the reference axis on a face containing the reference axis and that forms the angle with the reference axis and said contact point detecting means detects a point being farthest from the line to be used for calculation as the contact point from the plurality of points.

13. The fabrication aiding apparatus according to claim 12, wherein said detecting range input accepting means accepts an input of a detecting range in a direction surrounding the reference axis.

14. A fabrication aiding method to be applied to a fabrication aiding apparatus that aids fabrication of a dental prosthesis having shape data storing means to store three-dimensional shape data on a model of an abutment tooth to which the dental prosthesis is applied, the method comprising:
an angle input accepting, as executed by a processor of said apparatus, for accepting an input of specification of an angle;
a contact point detecting, as executed by a processor of said apparatus, for detecting, based on the three-dimensional shape data, three-dimensional position information about a contact point of said model with a line which is tangent with said model, and forms said angle with the reference axis on a face containing the reference axis; and
a margin line determining, as executed by a processor of said apparatus, for determining, based on coordinates of the contact point, three-dimensional position information of a margin line in said model of the abutment tooth.

15. A non-transitory computer-readable storage medium encoded with a computer program to be executed by a computer making up a fabrication aiding apparatus to aid fabrication of a dental prosthesis, wherein said fabrication aiding apparatus comprises:
shape data storing means to store three-dimensional shape data on a model of an abutment tooth to which the dental prosthesis is applied,
wherein said non-transitory computer-readable storage medium encoded with the computer program makes said computer function as angle input accepting means to accept an input of specification of an angle, function as contact point detecting means to detect, based on the three-dimensional shape data, three-dimensional position information about a contact point of said model with a line which is tangent with said model, and forms said angle with the reference axis on a face containing the reference axis, and function as margin line determining means to determine, based on coordinates of the contact point, three-dimensional position information of a margin line in said model of said abutment tooth.

16. A fabrication aiding apparatus, comprising:
shape data storing means to store three-dimensional shape data on a model of an abutment tooth to which a dental prosthesis is applied;
angle input accepting means to accept an input of specification of an angle;
detecting range input accepting means to accept an input of a detecting range in a direction of a reference axis;
contact point detecting means to detect, based on the three-dimensional shape data, three-dimensional position information about a contact point; and
margin line determining means to determine, based on coordinates of the contact point, three-dimensional position information of a margin line in said model of said abutment tooth,
wherein said contact point detecting means determines a line to be used for calculation that exists on a side of said model being outer than a plurality of points of said model that belongs to a detecting range in the direction of the reference axis on a face containing the reference axis and that forms the angle with the reference axis and said contact point detecting means detects a point being nearest from the line to be used for the calculation as the contact point from the plurality of points.

* * * * *